US011596948B2

(12) United States Patent
Lynn Hill

(10) Patent No.: US 11,596,948 B2
(45) Date of Patent: Mar. 7, 2023

(54) COATED ARTICLES FOR BLOOD COAGULATION TESTING AND METHODS OF PREPARING THE SAME

(71) Applicant: enicor GmbH, Munich (DE)

(72) Inventor: James Lynn Hill, Feldafing (DE)

( * ) Notice: Subject to any disclaimer, the term of this patent is extended or adjusted under 35 U.S.C. 154(b) by 428 days.

(21) Appl. No.: 16/348,056

(22) PCT Filed: Nov. 17, 2016

(86) PCT No.: PCT/EP2016/078081
§ 371 (c)(1),
(2) Date: May 8, 2019

(87) PCT Pub. No.: WO2018/091099
PCT Pub. Date: May 24, 2018

(65) Prior Publication Data
US 2019/0275515 A1    Sep. 12, 2019

(51) Int. Cl.
| | | |
|---|---|---|
| B01L 3/00 | (2006.01) | |
| C09D 133/20 | (2006.01) | |
| G01N 33/49 | (2006.01) | |
| A61L 33/06 | (2006.01) | |

(52) U.S. Cl.
CPC ............ B01L 3/5082 (2013.01); A61L 33/06 (2013.01); B01L 3/508 (2013.01); C09D 133/20 (2013.01); G01N 33/4905 (2013.01); *B01L 2200/143* (2013.01); *B01L 2300/163* (2013.01)

(58) Field of Classification Search
None
See application file for complete search history.

(56) References Cited

U.S. PATENT DOCUMENTS

| | | | | |
|---|---|---|---|---|
| 4,472,357 A | * | 9/1984 | Levy | B01L 3/5453 206/459.5 |
| 5,223,227 A | * | 6/1993 | Zuckerman | G01N 11/162 422/547 |
| 5,510,155 A | * | 4/1996 | Williams | B05D 7/02 427/532 |
| 2006/0034734 A1 | * | 2/2006 | Schubert | B29C 59/14 422/430 |

(Continued)

FOREIGN PATENT DOCUMENTS

| | | |
|---|---|---|
| EP | 1199104 A2 | 4/2002 |
| FR | 2555074 A1 | 5/1985 |

(Continued)

OTHER PUBLICATIONS

Venter, J. S., Database WPI Week 1 99126, Thomson Scientific, London, GB; (7 AN 1991-193475 & ZA 8 906 115 A (Stiroclad MFR Distr) Apr. 24, 1991.

(Continued)

*Primary Examiner* — Matthew D Krcha
(74) *Attorney, Agent, or Firm* — Sunstein LLP

(57) ABSTRACT

The present invention provides a coated article, which can be used in in-vitro diagnostics, in particular in the diagnostic testing of body fluids, such as in blood coagulation testing. The coated article is made of a polymer material and coated with a polymer material, which may be the same or different. The present invention furthermore provides a method of preparing such a coated article and a method of performing such diagnostics, e.g. coagulation analysis.

16 Claims, 13 Drawing Sheets

(56) References Cited

U.S. PATENT DOCUMENTS

| | | | | |
|---|---|---|---|---|
| 2010/0234524 A1* | 9/2010 | Coulson | ............... | B01L 3/50 |
| | | | | 524/560 |
| 2011/0151491 A1* | 6/2011 | Dennis | ............... | G01N 21/17 |
| | | | | 435/13 |
| 2011/0318777 A1* | 12/2011 | Kim | ............... | C12M 33/04 |
| | | | | 435/39 |

FOREIGN PATENT DOCUMENTS

| | | | | |
|---|---|---|---|---|
| GB | 1335209 A | * | 10/1973 | ........... B01D 53/025 |
| WO | WO 98/58690 | | 12/1998 | |

OTHER PUBLICATIONS

European Patent Office, Examiner H. Van den Bulcke, Examination Report dated Jul. 27, 2020 (application No. 16805991.3).
European Patent Office, Examiner Van den Bulcke, Examination Report dated Nov. 25, 2021 (application No. 16805991.3).

* cited by examiner

A

B

COATED ARTICLES FOR BLOOD COAGULATION TESTING AND METHODS OF PREPARING THE SAME

The present invention relates to the field of in-vitro diagnostics, in particular to the diagnostic testing of body fluids, such as blood samples. More specifically, the present invention relates to coated articles, which can be used in the diagnostic testing of body fluids, in particular in blood coagulation testing. The present invention also relates to a method of preparing such a coated article and to a method of coagulation testing using such a coated article.

The coagulation of blood is a highly complex process, starting with liquid blood and ending with the formation of a solid clot. It is an important part of hemostasis, i.e. the cessation of blood loss from a damaged vessel, wherein a damaged blood vessel wall is covered by a blood clot to stop hemorrhage and aid repair of the damaged vessel. Disorders in the coagulation balance can lead to increased hemorrhage and/or thrombosis and embolism.

In a normal individual, coagulation is initiated within about 20 seconds after an injury occurs to the blood vessel damaging the endothelial cells. Platelets immediately form a hemostatic plug at the site of injury. This process is called primary hemostasis. Secondary hemostasis follows if plasma components called coagulation factors respond in a complex cascade to finally form fibrin strands to strengthen the platelet plug.

The coagulation cascade of secondary hemostasis has two pathways, the Contact Activation pathway (formerly known as the Intrinsic Pathway) and the Tissue Factor pathway (formerly known as the Extrinsic pathway) that lead to fibrin formation. It was previously thought that the coagulation cascade consisted of two pathways of equal importance joined to a common pathway. It is now known that the primary pathway for the initiation of blood coagulation is the Tissue Factor pathway. The pathways are a series of reactions, in which a zymogen of a serine protease and its glycoprotein co-factor are activated to become active components, which are then able to catalyze the next reaction in the cascade. Coagulation factors are generally indicated by Roman numerals from I-XIII, with a lowercase 'a' appended to indicate the activated form. Thereby, a fibrin clot is formed, which strengthens the platelet plug.

Accordingly, in the case of injuries or inflammations the process of blood clotting can be activated by either intrinsic or extrinsic factors, e.g. tissue factor (TF) or Hagemann factor (F XII). Both activation channels are continued in a common branch of the cascade resulting in thrombin formation (FIG. 1). The thrombin itself finally initiates the formation of fibrin fibers, which represent the protein backbone of blood clots. Thrombin further activates thrombocytes, which are incorporated into the fibrin backbone (FIG. 2,3). Erythrocytes are only passively interweaved into the clot.

However, to avoid thrombosis and embolism, the formation of fibrin clots is tightly controlled. The fibrin clot, i.e. the product of coagulation, is broken down in a process called fibrinolysis. Accordingly, fibrinolysis prevents blood clots from growing and becoming problematic. In fibrinolysis, the enzyme plasmin plays a major role, since plasmin cuts the fibrin mesh at various places, leading to the production of circulating fragments that are cleared by other proteases and/or by the kidney and/or liver. Plasminogen is converted to active plasmin by tissue plasminogen activator (tPA) and urokinase, thereby allowing fibrinolysis to occur.

The detection of normal or decreased functionality of these coagulation and/or fibrinolysis components is important in order to assess patients' hemostasis disorders. If a hemostasis disorder is identified, a selected therapy can be applied for example to stop a bleeding.

Several methods of measuring the coagulation characteristics of blood are known. Some of such devices attempt to simulate the natural flow of blood in the veins and arteries of a living subject, while other measurement techniques are performed in static blood volumes.

An accurate measurement of the ability of a patient's blood to coagulate in a timely and effective fashion is crucial to certain surgical and medical procedures. Rapid and accurate detection of abnormal coagulations is also of particular importance with respect to appropriate treatment to be given to patients suffering from clotting disorders. Often the condition of such patients makes it necessary to administer blood components, anti-coagulants, certain fibrinolytic agents, anti-platelet agents, or compounds inducing the reverse effects of said agents. In these cases, the treatment dose can be adapted to the extent of a clotting disorder previously determined.

Measurements of blood clotting are provided by various devices, for example as described in detail in U.S. Pat. No. 5,777,215 A, in U.S. Pat. No. 6,537,819 B2, and in U.S. Pat. No. 8,383,045 B2. These devices measure the mechanical properties of the clot throughout its structural development. These systems are summarized under the term "viscoelastic methods", as they continuously detect viscoelastic properties of the blood clot while its formation and lysis. Viscoelastic measurements of clotting blood are commonly also referred to as thromboelastography (TEG) measurements.

In thrombelastography analyses, the fibrin backbone creates a mechanical, elastic linkage between the surfaces of two measurement articles, such as (i) a blood-containing cuvette and (ii) a probe plunged therein (FIG. 4). The shear modulus of this elastic connection can then be continuously monitored by rotating the probe within a small angle range and measuring the counteracting torque induced by the fibrin network as disclosed in detail for example in U.S. Pat. No. 5,777,215. A proceeding coagulation process induced by adding one or more activating factor(s) can thus be observed. In this way, various deficiencies of a patient's haemostatic status can be revealed and used for proper medical intervention (FIG. 5). In more general terms, it is a common feature of all methods used in coagulation diagnosis that the blood clot is formed between two measurement articles, wherein one of those measurement articles is typically fixed whereas the other is typically moving, such as the probe and the cuvette typically used in blood coagulation measurements. The elasticity of the blood clot formed between the fixed and the moving measurement article influences in particular the movement of the moving measurement article and can thus be assessed. Accordingly, coagulation measurement methods typically determine the blood clot's ability to couple the two measurement articles.

However, the measurement can only be evaluated as long as the fibrin network is sufficiently bound to the surfaces of said measurement articles. If the fibers tear off even partly, the disturbed measurement becomes hard to interpret because of interference between this effect and the pathologic pattern of hyperfibrinolysis (FIG. 6). Unfortunately, such tear-offs of the fibrin network can occur in the case of increased thrombocyte concentrations (well above 300.000/l) as observable for example in the blood of multi-trauma patients. In these patients the strength of the blood clot is enhanced and this can lead to too strong forces on the plastic surface, which can tear the clot off the material.

Although the original cup and pin material used for thromboelastometry during the fourties until the seventies was stainless steel, which was cleaned and reused, most of these devices were later exchanged by disposable items made of plastic in order to avoid cumbersome cleaning processes between the measurements. Such plastic items are typically economically produced by injection moulding or similar techniques. However, the adhesion strength of blood clots to the surface of such plastic items is mostly insufficient to avoid the problems described above. Therefore, an enhancement of the blood-clot adhesion strength would improve the therapeutic security considerably.

U.S. Pat. Nos. 4,148,216 and 5,223,227 describe disposable cups and pins for the use in thromboelastography (TEG) measurements. U.S. Pat. No. 5,223,227 discloses a production process for cup and pin material, which involves a roughening process of the moulds used for the injection moulding of the cups and pins. Roughening of the mould is the common strategy for enhancing the surface roughness of plastic parts produced by injection moulding. U.S. Pat. No. 5,223,227 describes mechanically roughening of the mould by sandblasting. However, the approach of roughening the mould to roughen the surface of the cup and pin to thereby enhance the adhesion of blood on the surface of the cup and the pin has several disadvantages: The blood-plastic interaction takes place especially in a microscopic range of the single plastic and of the fibrin molecules. In contrast, the roughness produced by the injection moulding process is in a much larger range. Therefore, the plastic surfaces produced by injection moulding provide only a limited adhesion of the blood clot. Although this may be sufficient for the analysis of a "normal" healthy blood sample, it is inadequate when factors are present in the blood, which compete with the adhesion of fibrin onto the plastic surfaces. In order to overcome this disadvantage, EP 1 627 725 suggests a plasma treatment process to improve adhesion strength in in-vitro blood coagulation analysis, i.e., the viscoelastic (also called thrombelastographic) testing of the shear modulus of clotting/clotted blood. However, in-production testing of the efficiency and regularity of the plasma-treatment process is rather difficult: either a test substance contaminates the treated surface (e.g., when applying a standard dye-drop test to measure increased hydrophilic behavior), or the test method is uneconomically costly and complex (e.g., when applying atomic force microscopy to detect structural modifications). With increasing demands for in-process quality assurance, a method with better testability of the modification efficiency is therefore needed.

In view of the above, it is the object of the present invention to overcome the drawbacks of current measurement articles for coagulation testing outlined above. In particular, it is an object of the present invention to provide a measurement article and a method of producing the same, which (i) achieves sufficient blood adhesion on its surface and (ii) whose quality can be controlled in an easy and cost-efficient way. In particular, it is an object of the present invention to employ a coating with special chemical substances in a way that considers the unique requirements of medical disposables regarding diagnostic result precision, the special application in thrombelastography diagnostics, the demands for in-process quality control, and the need for large-volume production (high part numbers). It is also an object of the present invention to provide a method to improve the adhesion strength of coagulating/coagulated blood on polymer surfaces by increasing the surface interaction of blood-inherent components like fibrin/fibrinogen and thrombocytes. In particular, it is an object of the present invention to provide measurement articles, which provide higher diagnostic specificity due to less misinterpretations of measurements (e.g., for patients with increased thrombocyte content) and in better significance of special tests (e.g., hyperfibrinolysis diagnosis).

The above objects are achieved by means of the subject-matter set out below and in the appended claims.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

Coated Article

In a first aspect the present invention provides an article for contacting coagulating and/or coagulated blood components made of a polymer material comprising a polymer, wherein the article is at least partially coated with a coating material comprising a polymer and/or a resin.

Such an article provides improved adhesion strength of coagulating and coagulated blood on polymer surfaces by increasing the surface interaction of blood-inherent components like fibrin/fibrinogen and thrombocytes. Thereby, irreversible effects of special chemical coatings applied to the surface of the article are utilized. Hence, the coating can provide polymeric surfaces with differently modified blood-adhesion properties by individual regulation of the coating characteristics. Moreover, the coating-based improvements of the blood clot adhesion result in higher diagnostic specificity due to less misinterpretations of measurements (e.g., for patients with increased thrombocyte content) and in improved discrimination between healthy and pathologic patients in hyperfibrinolysis diagnosis.

In addition, in the article according to the present invention relevant properties of the article, which are provided by the polymer material employed for manufacturing of the article (i.e. the polymer material of which the article is made of, i.e. the article's body typically consists of said polymer material), such as mechanical stability, melting point, price, weight, durability, flexibility etc., become independent from the required properties of article's surface. Instead, the 'surface properties' are solely defined by the coating material. Accordingly it is not necessary to find a material, which provides both, sufficient "body" and "surface" properties, and which usually represents a "compromise" between both. Therefore, the present invention allows to choose the optimum polymer material (to manufacture the article's body) without considering any surface properties thereof—and to choose the optimum surface (coating) material, which provides sufficient adhesion to coagulating and coagulated blood. For example, for the article's body a polymer material can be chosen, which requires lower cycle times for injection-molding, less hardened tools for milling, less material use, lower material prices, etc., and which is thus more cost-effective. For example, for the article's body a lightweight polymer material can be chosen. For example, for the article's body a polymer material can be chosen, which provides increased mechanical stability, durability, and/or flexibility. On the other hand, the coating material can be independently chosen such that it provides optimum blood adhesion.

Furthermore, quality testing of the article according to the present invention can be performed fast and easy, in particular by nondestructive testing methods such as by simple optical methods, for example by including (usually not otherwise functional) dyes or other particles in the coating material.

In general, the adhesion of coagulating and coagulated blood to surfaces is basically determined by the attractive forces between the outer molecular layer of the surface and those blood components that contribute to clot formation. The main components are on the one hand fibrin fibers built from fibrinogen proteins and on the other hand embedded thrombocytes (also called platelets), which are complete biological cells. The interaction forces of proteins and cells with polymeric surfaces are highly different from those of paints or lacquers. Therefore, technical coatings used to improve the adhesion of inorganic/synthetic materials, such as paint, on (polymer) surfaces, such as plastic, are not appropriate to improve the adhesion of blood to such surfaces.

The literature on blood component/(polymer) surface interaction is predominantly directed to detailed examinations of protein adsorption and/or platelet adhesion to different surfaces. The underlying mechanisms are highly complex, since several parallel or concurring processes are apparent (see, e.g., Soderquist & Walton, 'Structural changes in proteins adsorbed on polymer surface', *Journal of Colloid and Interface Science*, vol. 75(2), pp. 386-397, 1980; Tanaka et al., 'Blood compatible aspects of poly(2-methoxyethylacrylate) (PMEA)—relationship between protein adsorption and platelet adhesion on PMEA surface'; *Biomaterials*, vol. 21(14), pp. 1471-1481, 2000; Kim et al., 'Platelet adhesion to polymer surfaces', *ASAIO Journal*, vol. 20(1), pp. 449-455, 1974). In particular, the following underlying principles were identified: a) fibrinogen adsorption is not steady, but temporarily variable; b) fibrinogen adsorption is accompanied by strong conformational changes depending on the surface properties; c) fibrinogen adsorption is concurring with the adsorption of other blood-contained proteins such as albumin or globulin; d) fibrinogen adsorption is interacting with platelet adhesion; and e) platelet adhesion is also accompanied by strong conformational changes depending on the surface properties. In addition it is not yet known whether the mechanisms of fibrinogen adsorption are identical to fibrin adsorption (fibrinogen is the precursor of fibrin, and during blood clotting thrombin triggers polymerization of fibrinogen to form fibrin). In summary, at present no theoretical approach appears to exist to deduce an optimum surface coating to enhance blood clot adhesion to (polymeric) surfaces from the existing scientific knowledge.

The "article" may consist of one or more elements (parts). Preferably the article is a one-pieced article. Preferably, the body of the article is produced by typical mass-production plastic article procedures, such as injection molding, press molding, extrusion molding, milling, cutting, and/or swiveling. Preferably, the body of the article is produced by molding, such as injection molding, press molding, or extrusion molding. Most preferably, the body of the article is produced by injection molding.

Preferably, the article is a disposable article, i.e. an article, which is intended to be used only once. Thereby, cumbersome cleaning processes after blood contact are avoided.

The article may be any article, which can be (is) brought in contact with coagulating and/or coagulated blood components/blood. Preferably the article is used in coagulation testing, such as a part/element of a device used in coagulation testing, such as a viscoelastic measurement apparatus. Such a viscoelastic measurement apparatus is preferably a device as described in U.S. Pat. No. 5,777,215 A or in U.S. Pat. No. 6,537,819 B2. Another preferred example of an apparatus suitable for performing a viscoelastic analysis is schematically shown in FIG. 4.

In a preferred embodiment, the article is a measurement cup, such as a cuvette or a test cell, in particular to be used in coagulation testing, such as in viscoelastic measurement. As used herein, a "measurement cup" (also referred to as "cup", "cuvette" or "test cell") is a cup that receives the sample to be measured in the viscoelastic test (e.g., blood or blood components; cf. FIG. 4). Preferably, the measurement cup has a cylindrical or tapered shape. The measurement cup, in particular the cylindrical or tapered measurement cup, preferably comprises (i) an upper open end that allows insertion of a pin prior to a viscoelastic measurement; and (ii) a closed lower end designed to receive the sample. Preferably, the upper open end of the measurement cup and the closed lower end of the measurement cup have a circular shape. It is also preferred that the upper open end of the measurement cup has a diameter from 5 to 10 mm. Moreover, it is also preferred that the diameter of the (circular) upper open end of the measurement cup is not smaller than the diameter of the (circular) closed lower end. Preferably, the measurement cup has a cylindrical shape, whereby the diameter of the (circular) upper open end of the measurement cup and the diameter of the (circular) closed lower end of the measurement cup are about the same size. It is also preferred that the measurement cup has a tapered shape, whereby the diameter of the (circular) upper open end of the measurement cup is larger than the diameter of the (circular) closed lower end of the measurement cup. Preferably, the closed lower end of the measurement cup has no sharp edge along the border to the (cylindrical) sidewall of the measurement cup.

In another preferred embodiment the article is a probe, such as a pin, or a sleeve for a pin or probe, in particular to be used in coagulation testing, such as in viscoelastic measurement, for example a pin or a sleeve for a pin of a device used in coagulation testing. The term "pin" as used herein (also referred to as "measurement pin" or "probe") refers to an element for performing a viscoelastic test (cf. FIG. 4). Typically, for performing a viscoelastic test the sample to be tested, e.g. a (whole) blood sample, is provided in the measurement cup. For the viscoelastic test, typically a pin is dipped into the cup, thereby typically contacting the sample, e.g. a (whole) blood sample. Preferably, the pin is immerged into the sample, e.g. a (whole) blood sample. Preferably, the pin used to perform the viscoelastic measurement has a radius of similar size, preferably of about the same size, more preferably of the same size, along its outer edge between lower end and cylindrical sidewall as the cup has along its inner edge between lower end and cylindrical sidewall (cf. FIG. 4).

The detection of the characteristic parameters of the sample, e.g. the blood forming a clot, is typically based on the (mechanical) coupling of cup and pin which is established by the formation of e.g. a clot (cf. FIG. 4). Typically, the measurement is performed in a viscoelastic measurement apparatus as described herein, wherein either the pin is moved, preferably rotated, whereas the cup is stationary at the beginning or stays stationary throughout the measurement—or the cup is moved, preferably rotated, whereas the pin is stationary at the beginning or stays stationary throughout the measurement. After the formation of, for example, a clot between cup (cuvette) and pin, the clot itself is stretched by the movement of the pin relative to the cup or of the cup relative to the pin. For example, the cup may rotate and the pin is stationary at the beginning, but able to rotate as well. Upon clot formation in this case the pin may typically start to rotate, which can be measured. In a preferred example, the pin rotates and the cup stays stationary throughout the measurement, whereby upon clot formation the initial unrestricted rotation of the pin starts to encounter increasing impedance as the clot strength increases, which is typically measured, e.g. by detection by an optical system.

A "sleeve" for a pin typically covers the pin's tip, which can come in contact with blood or blood components, and is typically used for such pins, which are for repeated use (no disposables) and are made of non-polymeric material, such as metal (e.g., stainless steel). Therefore, by using a (disposable) "sleeve" for the pin cumbersome cleaning of the pin itself can be avoided.

As used herein, "coagulating and/or coagulated blood components" refers to any (physical) component of coagulating and/or coagulated blood, such as any kind of blood cells, fibrin, serum etc., which is present during or after blood coagulation. However, since at least the blood's fibrin fibers and/or platelets are required for adhesion of the coagulating and/or coagulated blood to a surface, the term "coagulating and/or coagulated blood components", as used herein, includes at least fibrin and/or platelets, and optionally one or more additional component of coagulating and/or coagulated blood. Preferably the article is (used) for contacting whole blood, i.e. blood as obtained from a donor, which is in particular unprocessed blood. Since coagulation is desired, the addition of an anticoagulant to the blood is preferably avoided. Therefore, it is preferred if the article is (used) for contacting coagulating and/or coagulated blood. The term "coagulation" ("coagulating", "coagulated") is synonymously used herein with "clotting" and refers to the process by which blood changes from a liquid to a gel, in particular forming a blood clot. Preferred blood components are mammalian blood components, more preferably human blood components. Accordingly, preferred blood is mammalian blood, more preferably human blood.

As used herein "made of a polymer material" means that the main component of the article's body is typically said polymer material. A "main component" is the component with the highest percent by weight in the article's body. Typically, the main component accounts for more than 50% by weight of the article's body, more preferably for at least 70% by weight of the article's body, even more preferably for at least 80% by weight of the article's body, still more preferably for at least 90% by weight of the article's body, and most preferably for at least 95% by weight of the article's body. The article's "body" as used herein refers to the article without the coating material. Accordingly, an article according to present invention preferably consists of a "body" and the coating material. However, further elements/components may optionally be added to/included in an article according to the present invention, in particular after/during coating. Most preferably, the article's body consists essentially of the polymer material.

As used herein, the term "polymer material" is used throughout the present application for the material, of which the article's body is made as described above. The polymer material comprises a polymer. The polymer material may also comprise one or more further substances, which are not polymers. The polymer material may also comprise two or more (distinct) polymers.

As used herein (i.e. throughout the present application) a "polymer" is typically a macromolecule (i.e. a large molecule), which comprises many repeated subunits (monomers). Preferably, the polymer is a synthetic polymer. A "synthetic" polymer is a polymer, which is synthesized (polymerized) synthetically. Preferably, the synthetic polymer cannot be produced by living organisms (in contrast to biopolymers such as polynucleotides, polypeptides, silk, wool, cellulose, starch and the like). The polymer may be composed of only one single type repeated subunits (one single type of monomers). The polymer may also be composed of two or more types of repeated subunits (two or more types of monomers). A polymer composed of two or more types of repeated subunits (two or more types of monomers) is also referred to as copolymer. Preferred copolymers include bipolymers (two types of monomers), terpolymers (three types of monomers) and quaterpolymers (four types of monomers). Based on the arrangement of the different types of monomers in the copolymer, preferred copolymers include alternating copolymers (with regular alternating monomers), periodic copolymers (with different monomers arranged in a repeating sequence), statistical copolymers (in which the sequence of monomer residues follows a statistical rule), random copolymers, block copolymers (which comprise two or more homopolymer subunits linked by covalent bonds), and graft (or grafted) copolymers (which contain side chains that have a different composition or configuration than the main chain). In general, to customize the properties of a polymer, different molecular groups may "hang" from the backbone (for example, they may be "hung" as part of the monomers before the monomers are linked together to form the polymer chain). The structure of these "side chains" influence the properties of the polymer. This fine tuning of the repeating unit's molecular structure influences the properties of the polymer.

A preferred polymer material is plastic. The term "plastic" as used herein refers to a composition comprising an organic polymer. Plastics may optionally also comprise additional substances. Plastics are typically synthetic, however, bioplastics (in particular made substantially from renewable plant materials such as cellulose and starch) gain increasing importance. Plastics are typically malleable at elevated temperatures and can be molded into solid objects, in particular by heating, molding and cooling. Preferably, plastics are synthetic, more preferably plastics are derived from petrochemicals. Preferably, the organic polymer of the plastic is based on chains of carbon atoms alone or with oxygen, sulfur, and/or nitrogen. Preferably, the plastic comprises further organic or inorganic compounds blended in, such as additives. The amount of additives may range from zero percentage (i.e. plastic consisting of one or more organic polymer(s)) to more than 50% by weight. Preferably, the amount of additives is 0-50% by weight, more preferably 5-40% by weight, even more preferably 10-30% by weight, still more preferably 15-25% by weight and most preferably about 20% by weight. Preferred additives include fillers, plasticizers and colorants. Fillers preferably improve performance and/or reduce production costs. For example, stabilizing additives include fire retardants to lower the flammability of the material. Preferred fillers are mineral in origin, e.g., chalk. Some fillers are more chemically active and are called reinforcing agents. Other preferred fillers include zinc oxide, wood flour, ivory dust, cellulose and starch. Plasticizers are oily compounds that confer improved rheology.

More preferably, the polymer material of which the article according to the present invention is made (i.e. the article's body as described above) is a mass-production compatible plastic, such as thermoplastics, thermoplastic elastomers, conventional elastomers, or duromers. Even more preferably, the polymer material comprises polymethylpentene (PMP) and/or methyl methacrylate acrylonitrile butadiene styrene (MABS).

Preferably, the article made of the polymeric material (i.e. the article's body as described above) is produced by injection molding, press molding, extrusion molding, milling, cutting, and/or swiveling. More preferably, the article made of the polymeric material (i.e. the article's body as described above) is produced by molding, such as injection molding, press molding, or extrusion molding. Most preferably, the article made of the polymeric material (i.e. the article's body as described above) is produced by injection molding.

As used herein "at least partially coated" means that at least a part of the surface of the article's body is covered with the coating material. Preferably, the article is completely coated, i.e. the entire surface of the article (i.e. the article's body) is covered with the coating material. Such articles can be easily obtained by simple and cost-effective coating procedures, for example by dipping the article into the coating composition. It is also preferred that the article is only partially coated, wherein "partially coated" means that at least that part or those parts of the article are coated, which are contacted by coagulating and/or coagulated blood (components) during the articles normal use. For example, if the article is a measurement cup, the coagulating and/or coagulated blood (components) typically contacts during its normal use the measurement cup's inside surface (i.e. the concave surface), whereas the measurement cup's outside surface (i.e. the convex surface) is typically not contacted by blood or blood components. Accordingly, in the case of a measurement cup "at least partially coated" means that at least the measurement cup's inside surface (i.e. the concave surface) is coated. It may be preferred that the article is only partially covered (e.g., for the measurement cup only the inside surface), in particular if the coating material is expensive. In particular, to improve blood adhesion it is usually not necessary to coat such parts of the article's surface, which are not in contact with blood during the article's normal (intended) use. To provide another example, if the article is a pin or a sleeve for a pin, typically only its apical part ("tip", e.g. convex surface) is intended for contact with blood, whereas its shaft is usually not intended for contact with blood. Accordingly, in the case of a pin or sleeve for a pin "at least partially coated" means that at least the apical part ("tip", e.g. convex surface) is coated, which may be obtained, e.g. by dipping only the apical part of the pin into the coating composition.

A "coating material", as used herein, is a material which covers the surface of an article (i.e. the surface of the article's body) at least partially. The coating is usually a very thin layer, e.g. no thicker than 1 mm, preferably no thicker than 0.5 mm, more preferably no thicker than 0.25 mm and most preferably no thicker than 100 µm. As used herein the "coating material" is typically distinct from the "coating composition". In particular, the "coating material" differs from the "coating composition" at least in that the "coating material" is typically solid, whereas the "coating composition" is typically liquid. The "coating material" is usually obtained by drying of the "coating composition". Accordingly, the solvent comprised by the "coating composition" may be partially or completely removed in the "coating material".

The coating material comprises a polymer, in particular as defined above, and/or a resin. Optionally, the coating material may also comprise further components, such as for example a dye or particles as described below.

A resin is typically a solid or highly viscous substance, which may be convertible into polymers. Preferably, the resin contains prepolymers with reactive groups. Resins may be mixtures of organic compounds. The term "resin" as used herein includes any polymer that is a basic material for plastics, organic coatings, or lacquers, prepolymers of thermosets (thermosetting polymers), and cured thermosets (e.g., epoxy resins, phenolic resins). The resin may be naturally occurring (or derived from a naturally occurring) or synthetic.

Preferably, the polymer and/or the resin comprised by the coating material is soluble in a liquid solvent. Thereby, a coating composition can be easily provided by dissolving the polymer and/or the resin in the liquid solvent. The coating composition may then be applied to the article's surface (or one or more parts thereof as described herein)

and, preferably, dried to obtain the coating material. More preferably, the polymer and/or the resin comprised by the coating material is soluble in a lower-risk solvent as described below. Even more preferably, the polymer and/or the resin comprised by the coating material is soluble in benzene or benzene derivatives (e.g., alkyl benzenes or polyalkyl benzenes); acetate or acetate derivatives (e.g., alkyl or polyalkyl acetates); alkanols or alkanol derivatives (e.g., alkandiols or cyclo alkanols); or naphtha or naphtha components. As used herein a "derivative" is derived from the reference compound by a (single) chemical reaction, e.g. a benzene derivative is derived from benzene by a (single) chemical reaction, an acetate derivative is derived from acetate by a (single) chemical reaction, etc. Most preferably, the polymer and/or the resin comprised by the coating material is soluble in xylene, ethylbutanol, chloroform and/or acetone. The polymer may also be soluble in DMSO (dimethyl sulfoxide). In particular, preferred polymers and/or resins comprised by the coating material are soluble in preferred solvents as described below, in the context of the coating composition according to the present invention.

Preferably, the coating material comprises at least one polymer, in particular as defined above. Preferably, the polymer comprised by the coating material is a polymer or a copolymer comprising one or more monomers selected from styrene monomers, (meth)acrylate monomers, (meth)acrylamide monomers, alkyl monomers, vinyl monomers, allyl monomers, carbonate monomers, aromatic monomers, olefin monomers, halogenolefine monomers, methylolefine monomers, urethane monomers, amide monomers, ester monomers and/or ether monomers.

Preferred coating compositions according to the present invention contain at least one polymer of the following groups: polystyrenes, polycarbonates, polymethacrylates, polyolefines, polyhalogenolefines such as polyfluorolefines, polymethylolefines, polyacetals, polyurethanes, polyamides, polyaramides, polyesters, polyethers, polyketones, or any (partially) substituted polymers thereof, or any (mixed co-polymers) of said non-substituted or (partially) substituted polymers. As used herein, the term "(partially) substituted polymers" refers to polymers, wherein at least one hydrogen or one functional group is replaced ("substituted") by another atom or molecule, such as a hydrogen or (another) functional group. A "functional group" is in particular a specific group (moiety) of atoms or bonds within molecules that are responsible for the characteristic chemical reactions of those molecules. The same functional group will typically undergo the same or similar chemical reaction(s) regardless of the size of the molecule it is a part of. The atoms of functional groups are linked to each other and to the rest of the molecule by covalent bonds. Preferred examples of functional groups include hydrocarbonyl groups, such as alkyl ($R(CH_2)_nH$), alkenyl ($R_2C=CR_2$), alkynyl ($RC\equiv CR'$), and phenyl (RPh ($RC_6H_5$)); groups containing halogens (halogen atoms), such as halo (RX), fluoro (RF), chloro (RCl), bromo (RBr), and iodo (RI); groups containing oxygen, such as hydroxyl (ROH), carbonyl (RCOR'), aldehyde (RCHO), haloformyl (RCOX), carbonate ester (RO-COOR), carboxylate ($RCOO^-$), carboxyl (RCOOH), ester (RCOOR'), methoxy ($ROCH_3$), hydroperoxy (ROOH), peroxy (ROOR), ether (ROR'), hemiacetal (RCH(OR')(OH)), hemiketal (RC(OR")(OH)R'), acetal (RCH(OR')(OR")), ketal (RC(OR")(OR''')R'), orthoester (RC(OR')OR")(OR''')), methylenedioxy (PhOCOPh), and orthocarbonate ester (C(OR)(OR')(OR")(OR''')); groups containing nitrogen, such as carboxamide ($RCONR_2$), primary amine ($RNH_2$), secondary amine ($R_2NH$), tertiary amine ($R_3N$), 4° ammonium ion ($R_4N^+$), primary ketimine (RC(=NH)R'), secondary ketimine (RC(=NR")R'), primary aldimine (RC(=NH)H), secondary aldimine (RC(=NR')H), imide ($(RCO)_2NR'$), azide ($RN_3$), azo (diimide; $RN_2R'$), cyanate (ROCN), isocyanate (RNCO), nitrate ($RONO_2$), nitrile (RCN), isonitrile (RNC), nitrosooxy (RONO), nitro ($RNO_2$), nitroso (RNO), oxime (RCH=NOH), and pyridyl ($RC_5H_4N$); groups containing sulfur, such as sulfhydryl (RSH), sulfide (RSR'), disulfide (RSSR'), sulfinyl (RSOR'), sulfonyl ($RSO_2R'$), sulfino ($RSO_2H$), sulfo ($RSO_3H$), thiocyanate (RSCN), isothiocyanate (RNCS), and carbonothioyl (RCSR'; RCSH); groups containing phosphorus, such as phosphino ($R_3P$), phosphono ($RP(=O)(OH)_2$), and phosphate ($ROP(=O)(OH)_2$; $HOPO(OR)_2$); and groups containing boron, such as borono ($RB(OH)_2$), boronate ($RB(OR)_2$), borino ($R_2BOH$), and borinate ($R_2BOR$).

For example, in a (partially) substituted polymer, at least one hydrogen may be substituted by a hydroxyl group, an amino group, an ether group, a carbonyl group, a halogen atom or any other functional group as described above.

More preferably, the polymer comprised by the coating material is a polymer or a copolymer comprising one or more monomers selected from styrene monomers, (meth)acrylate monomers, (meth)acrylamide monomers, carbonate monomers, amide monomers, and aromatic monomers; or any combined and/or (partially) substituted polymer thereof.

Preferably, the coating material comprises a styrene containing (co-)polymer. Styrene containing (co-)polymers dissolve more easily in lower-risk solvents like alkyl benzenes or alkyl acetates, as compared to other polymers.

Even more preferably, the polymer comprised by the coating material is selected from acrylonitrile butadiene styrene (ABS), methyl methacrylate acrylonitrile butadiene styrene (MABS), polystyrene (PS), high impact polystyrene (HIPS), poly(methyl methacrylate) (PMMA), polycarbonate (PC), polyamide (PA), and polyphenylene sulfide (PPS). Still more preferably, the polymer comprised by the coating material is selected from acrylonitrile butadiene styrene (ABS), methyl methacrylate acrylonitrile butadiene styrene (MABS), polystyrene (PS), high impact polystyrene (HIPS), polycarbonate (PC), polyamide (PA), and polyphenylene sulfide (PPS). Most preferably, the polymer comprised by the coating material is selected from methyl methacrylate acrylonitrile butadiene styrene (MABS), high impact polystyrene (HIPS), polycarbonate (PC), polyamide (PA), and polyphenylene sulfide (PPS).

Most preferably, the polymer comprised by the coating material is acrylonitrile butadiene styrene (ABS). Most preferably, the polymer comprised by the coating material is methyl methacrylate acrylonitrile butadiene styrene (MABS). Most preferably, the polymer comprised by the coating material is polystyrene (PS), in particular high impact polystyrene (HIPS). Most preferably, the polymer comprised by the coating material is poly(methyl methacrylate) (PMMA). Most preferably, the polymer comprised by the coating material is polycarbonate (PC). Most preferably, the polymer comprised by the coating material is polyamide (PA). Most preferably, the polymer comprised by the coating material is polyphenylene sulfide (PPS).

Preferably, the polymer comprised by the coating material is distinct from the polymer comprised by the polymer material. Thereby, the blood clot adhesion strength provided by the polymer material, of which the article's body is made, can be improved by using a polymer for the coating material, which provides increased blood clot adhesion strength. As shown by the present examples, polymer materials, of which the article's body may be made, may be, for example, the light-weight material polymethylpentene (PMP) or polyurethane (PU). Both materials provide only relatively weak blood clot adhesion strengths (as shown by the present examples). Coating materials comprising, for example, acrylonitrile butadiene styrene (ABS), methyl methacrylate acrylonitrile butadiene styrene (MABS), polystyrene (PS), high impact polystyrene (HIPS), poly(methyl methacrylate) (PMMA), polycarbonate (PC), polyamide (PA), or polyphenylene sulfide (PPS), which all provide higher blood clot adhesion strengths than PMP or PU (as shown by the present examples), therefore increase the article's blood clot adhesion strength. Accordingly, in a preferred embodiment the article (the article's body) is made of polymers, which form surfaces with low blood clot adhesion capabilities, such as PMP or PU (as shown in the present examples) or fluorinated polyolefines like polytetrafluorethylene (PTFE) (which are well-known to form surfaces with low adhesion capabilities) and the article is at least partially coated with a coating material comprising a polymer and/or a resin providing high blood clot adhesion capabilities, such as acrylonitrile butadiene styrene (ABS), methyl methacrylate acrylonitrile butadiene styrene (MABS), high impact polystyrene (HIPS), poly(methyl methacrylate) (PMMA), polycarbonate (PC), polyamide (PA), or polyphenylene sulfide (PPS) (as shown by the present examples).

However, it is also preferred that the polymer comprised by the coating material is the same as the polymer comprised by the polymer material. Even if the very same material is used as polymer material and as coating material, the blood clot adhesion strength is improved (as surprisingly shown by the present examples). Since the solvent's effect on blood clot adhesion strength is negligibly, as shown by the present examples, it is assumed (without being bound to this theory) that the distribution of the polymer plays a role. Preferably, if the polymer comprised by the coating material is the same as the polymer comprised by the polymer material, the article (i.e. the article's body) is obtained by molding, more preferably by injection molding, press molding, or extrusion molding, most preferably by injection molding. Preferably, if the polymer comprised by the coating material is the same as the polymer comprised by the polymer material, the coating material is applied by dipping the article (i.e. the article's body) into a coating composition or by filling the article (i.e. the article's body) with a coating composition, preferably followed by drying.

Preferably, the coating material comprises at least one resin as defined above. Preferred resins include synthetic resins as well as natural resins. Preferably, the resin is selected from epoxy resin, phenol resin, polyurethane resin and/or acrylate resin.

As used herein, "epoxy resins" are low molecular weight pre-polymers or higher molecular weight polymers which normally contain at least two epoxide groups. The epoxide group is also sometimes referred to as a glycidyl or oxirane group. A wide range of epoxy resins are produced industrially. The raw materials for epoxy resin production are today largely petroleum derived, although some plant derived sources are now becoming commercially available (e.g. plant derived glycerol used to make epichlorohydrin). Epoxy resins are typically polymeric or semi-polymeric materials, and as such rarely exist as pure substances, since variable chain length results from the polymerization reaction used to produce them. High purity grades can be produced for certain applications, e.g. using a distillation purification process. One downside of high purity liquid grades is their tendency to form crystalline solids due to their highly regular structure, which require melting to enable processing. Examples of epoxy resins include bisphenol A epoxy resins, bisphenol F epoxy resins, novolac epoxy resins, aliphatic epoxy resins, and glycidylamine epoxy resins.

Phenol resins (also referred to as "phenolic resins" or "phenol formaldehyde resins" (PF)) are typically synthetic polymers obtained by the reaction of phenol or substituted phenol with formaldehyde. Used as the basis for Bakelite, PFs were the first commercial synthetic resins (plastics). Preferred phenolic resins include novolacs and resoles. Both have high temperature stability up to 300°-350° C., high water and chemical stability. Phenolic resins are often dark-colored from yellow to dark red, and have an excellent price/performance profile.

Acrylate resins (also referred to as "acrylic resin") are a group of related thermoplastic or thermosetting plastic substances derived from acrylic acid, methacrylic acid or other related compounds. A preferred acrylic resin is polymethyl acrylate, which may be used in an emulsified form. Another preferred acrylic resin is polymethyl methacrylate (PMMA).

As described above, the coating material may optionally comprise further components in addition to the polymer and/or the resin. Preferably, the coating material comprises a dye, such as an absorptive and/or fluorescent dye, a phosphorescent dye, or an otherwise luminescent dye, for example coumarine, methylene blue, rhodamine, fluorescein, and luciferin. It is also preferred that the coating material comprises a particle enabling determination of the quality of the coating. Preferred particles include metal or other electrically conductive particles, and magnetic particles. Preferably, the dye and/or the particles are selected such that they enable high-speed and low-cost in-process inspection of the coating quality, e.g., by optical or other physical methods, such as detection by optical, electrical, or magnetic fields, for example by light reflection color changes, light image changes, X-ray image changes, fluorescence image changes, light emission wavelength changes, magnetic field changes, etc.

Coating Composition

In a further aspect, the present invention also provides a coating composition for coating an article for contacting coagulated blood or coagulated blood components made of a polymer material, wherein the coating composition comprises (i) a polymer and/or a resin; and
(ii) a solvent, which is capable of dissolving at least $1*10^{-6}$% v/v of the coating polymer and/or the coating resin and which forms a contact angle on the polymer material surface of the article of less than 90° when containing the coating polymer and/or resin; or a first solvent, which is capable of dissolving at least 0.1% v/v of the coating polymer and/or the coating resin and which forms a contact angle on the polymer material surface of the article of 90° or higher when containing the coating polymer and/or resin, and a second solvent in an amount of at least 20% of said first solvent, which forms a contact angle on the polymer material surface of the article of less than 90° and which has an at least 10% longer drying time than said first solvent.

Whether the contact angle on the polymer material surface of the article is (i) less than 90° or (ii) 90° or higher, can be determined by using common measurement devices for measuring the contact angle, such as "Drop Shape Analyzer DSA100" (Krüss GmbH, Hamburg, Germany); "OCA 15EC", "OCA25", "OCA50", or "OCA100/100 Micro" (all obtainable from DataPhysics Instruments GmbH, Filderstadt, Germany); or "Surftens UNIVERSAL", "SURFTENS automatic", "Surftens HL", or "Surftens WH 300" (all obtainable from OEG Gesellschaft für Optik, Elektronik & Gerätetechnik mbH, Frankfurt(Oder), Germany).

Typically, the polymer and/or the resin is dispersed or dissolved in the solvent. More preferably, the polymer and/or the resin is dissolved in the solvent. Accordingly, the coating composition is preferably a liquid, more preferably a homogenous liquid. A homogeneous coating composition results in a homogenous distribution of the polymer and/or the resin on the surface of the article for contacting coagulated blood or coagulated blood components made of a polymer material. This ensures (i) even distribution of the polymer across the complete coated area (without any "gaps") and (ii) avoidance of any bumps or unevenness, which may (negatively) influence/distort viscoelastic measurements performed by using the article.

The present invention provides a coating composition for obtaining an article according to the present invention as described above, namely by applying the coating composition to the article's body to obtain a coating material as described above. Accordingly, preferred embodiments of the article for contacting coagulated blood or coagulated blood components made of a polymer material, which is to be coated with the coating composition according to the present invention, correspond to preferred embodiments of the article according to the present invention (in particular the article's body as described above) as described above.

Moreover, since the coating material of the article according to the present invention is preferably obtained by drying a coating composition according to the present invention, the polymer and/or the resin comprised by the coating composition according to the present invention is preferably the same as the polymer and/or the resin comprised by the coating material as described above. Accordingly, preferred embodiments of the polymer and/or the resin comprised by the coating composition according to the present invention correspond to preferred embodiments of the polymer and/or the resin comprised by the coating material as described above.

For example, the coating composition comprises preferably at least one polymer, in particular as described above regarding the polymer comprised by the coating material. Preferably, the polymer comprised by the coating composition is a polymer or a copolymer comprising one or more monomers selected from styrene monomers, (meth)acrylate monomers, (meth)acrylamide monomers, alkyl monomers, vinyl monomers, allyl monomers, carbonate monomers, aromatic monomers, olefin monomers, halogenolefine monomers, methylolefine monomers, urethane monomers, amide monomers, ester monomers and ether monomers.

Preferably, the coating composition comprises at least one polymer or copolymer selected from polystyrenes, polycarbonates, polymethacrylates, polyolefines, polyhalogenolefines, polymethylolefines, polyurethanes, polyamides, polyesters, polyethers, any partially substituted polymers thereof, or any co-polymers thereof.

It is also preferred that the polymer comprised by the coating composition is a polymer or a copolymer comprising one or more monomers selected from styrene monomers, (meth)acrylate monomers, (meth)acrylamide monomers, carbonate monomers, amide monomers, and aromatic monomers.

Preferably, the coating composition comprises a styrene containing (co-)polymer. Styrene containing (co-)polymers dissolve more easily in lower-risk solvents like alkyl benzenes or alkyl acetates, as compared to other polymers.

Even more preferably, the polymer comprised by the coating composition is selected from acrylonitrile butadiene styrene (ABS), methyl methacrylate acrylonitrile butadiene styrene (MABS), polystyrene (PS), high impact polystyrene (HIPS), poly(methyl methacrylate) (PMMA), polycarbonate (PC), polyamide (PA), and polyphenylene sulfide (PPS). Still more preferably, the polymer comprised by the coating composition is selected from acrylonitrile butadiene styrene (ABS), methyl methacrylate acrylonitrile butadiene styrene (MABS), polystyrene (PS), high impact polystyrene (HIPS), polycarbonate (PC), polyamide (PA), and polyphenylene sulfide (PPS). Most preferably, the polymer comprised by the coating composition is selected from methyl methacrylate acrylonitrile butadiene styrene (MABS), high impact polystyrene (HIPS), polycarbonate (PC), polyamide (PA), and polyphenylene sulfide (PPS).

It is also preferred that the coating composition comprises at least one resin, in particular as described above regarding the resin comprised by the coating material. Accordingly, the resin is preferably selected from epoxy resin, phenol resin, polyurethane resin and/or acrylate resin as described above.

Typically, the necessary solvability of the polymer and/or the resin comprised by the coating composition in the solvent comprised by the coating composition depends on the physical properties of said solvent: To obtain homogeneous coatings, the final coating material after drying should have a thickness of at least 10 molecular layers, which corresponds to about 1 nm (at least). More preferred coatings result in a thickness of the coating material layer (after drying) of 100 nm to 100 µm. The layer thickness of the coating composition before drying determines the required ratio of dissolved polymer in the used solvent. For example, coating by dipping techniques usually results in coating composition layers of 1 to 500 µm thickness, basically depending on the viscosity and surface tension of the coating composition. Other coating techniques like spraying result typically in liquid layers of 1 to 100 µm thickness and are at least less sensitive to the viscosity of the coating composition. To create a coating material layer of 1 nm thickness (after drying) with a coating composition that forms a 500 µm thick liquid layer (before drying), the solvent is preferably able to dissolve only $2*10^{-6}$% v/v (volume percent) of the polymer and/or the resin comprised by the coating composition. To create a coating material layer of 1 µm thickness (after drying) with a coating composition that forms a 2 µm thick liquid layer (before drying), the solvent preferably dissolves at least 10% v/v (volume percent) of the polymer and/or the resin comprised by the coating composition. The numbers indicate that the required solubility range starts around $10^{-6}$% v/v and may end near 100%, depending on the employed solvent and coating technique. Since the mass densities of solvents (typically ranging between 0.5 and 1.5 g/cm$^3$) and polymers (typically ranging between 0.8 and 2 g/cm$^3$) are quite identical, rather similar numbers are obtained when using weight percent (% w/w).

Preferably, the solvent comprised by the coating composition is a lower-risk solvent. As used herein, a "lower-risk solvent" is associated with fewer risks regarding environmental hazards, health hazards (for the employed personnel processing the coating), or explosion/inflammation hazards. In particular, the concentration of "lower risk solvents" in the air of a typical room (having a size of at least 20 m$^3$) does not exceed the recommended maximum concentration when applied as coating solvent to a typical lot size of articles to be coated (e.g., 10.000 articles or more) during an 8 hour shift. Recommended maximum concentrations considering the risks of inflammation/explosion or health hazards can typically be found in corresponding data bases (e.g., GESTIS Stoffdatenbank, http://gestis.itrust.de) or in safety data sheets. For example, the recommended maximum concentration of xylene is 221 mg/m$^3$ (with a vapor pressure of 8 hPa at 20° C.), the recommended maximum concentration of ethylacetate is 1500 mg/m$^3$ (with a vapor pressure of 98.4 hPa at 20° C.), and the recommended maximum concentration of benzene is 3.25 mg/m$^3$ (with a vapor pressure of 98.4 hPa at 20° C.). According to its low vapor pressure, xylene does typically not concentrate in the air of a typical room size above the recommended maximum concentration when applied as coating solvent to a typical lot size of articles as described above. Ethylacetate has a more than ten times higher vapor pressure, but also a seven times higher recommended maximum concentration. Accordingly, both solvents are "lower risk solvents" as described herein. Benzene, in contrast, has a more than ten times higher vapor pressure than xylene, but less than one tenth of recommended maximum concentration. Accordingly, benzene would concentrate in the air of a typical room size at a higher value than its maximum recommended concentration when applied as coating solvent to a typical lot size of disposables as described above. Therefore, benzene is no "lower risk solvent" (but may, instead, be regarded as "higher risk solvent"). Since lower risk solvents do typically not require additional safety measures, such as air exhaust systems and inhalation protection, the use of lower-risk solvents increases the efficiency of the production process.

Preferably, the solvent is volatile and, thus, evaporates during coating and/or during a subsequent drying step. As used herein, the term "volatile" means a high vapor pressure at ordinary room temperature (e.g., about 20° C. or about 22° C.). The high vapor pressure results from a low boiling point, which causes large numbers of molecules to evaporate or sublimate from the liquid or solid form of the compound and enter the surrounding air, a trait known as volatility. Preferably, a volatile solvent has an initial boiling point less than or equal to 250° C. (482° F.) measured at a standard atmospheric pressure of 101.3 kPa.

Preferably, the solvent is a non-polar solvent or a solvent with low polarity only. Due to the high polarity of a highly polar solvent like DMSO, a corresponding coating composition does usually not evenly coat on other polymer surfaces, but the coating composition might form small droplets. If these droplets dry out the solvent, the coating material may form little bumps on the surface and no evenly distributed coating layer is obtained. This highly-complex problem of 'wettability' is connected to the contact angle that forms if a small droplet of a liquid (e.g., solvent) is put onto a solid surface: if the tangent angle of the droplet surface on the contact point to the solid surface is 90° or higher, a certain amount of that liquid cannot form a homogeneous layer on said surface, but will always shrink to small droplets. This problem can be at least partially avoided by adding at least one further solvent to the coating composition, which forms a contact angle of less than 90° on the employed polymer material, of which the article's body is made, and has a longer drying time than the first solvent. The required ratio between both solvents can be obtained by measuring the contact angle of the coating composition, which must be below 90°.

Accordingly, the coating composition comprises one or more solvents capable of solving the polymer(s) and/or resin(s) comprised by the coating composition sufficiently. Preferred solvents, which form a contact angle on the polymer material, of which the article's body is made, of less than 90° are preferably selected for example from the group of benzene and benzene derivates, in particular alkyl benzenes (e.g., methylbenzene, ehtylbenzene, propylbenzene, etc.) or polyalkylbenzenes (e.g., methylethylbenzene, methyl-propylbenzene, etc.). Another group of preferred solvents are acetates, in particular alkyl acetates (e.g., methyl aceteate, ethyl acetate, propyl acetate, etc.) or polyalkyl acetates (e.g., methylethyl acetate, methylpropyl acetate, etc.). Preferred solvents further comprise the group of alkanols, more preferred alkylalkanols (e.g., methylmethanol, methylethanol, methylpropanol, methylbutanol, etc.), alkandiols, or cycloalkanols (e.g., cyclobutanol, cyclopentanol, cyclohexanol, cycloheptanol, etc.). The group of preferred solvents further comprise any derivatives and isomeric forms of the above mentioned solvents. As used herein a "derivative" is derived from the reference compound by a (single) chemical reaction, e.g. a benzene derivative is derived from benzene by a (single) chemical reaction, an acetate derivative is derived from acetate by a (single) chemical reaction, etc.

More preferably, the coating composition comprises at least one solvent selected from benzene or benzene derivatives (e.g., alkyl or polyalkyl benzenes); acetate or acetate derivatives (e.g., alkyl or polyalkyl acetates); alkanols or alkanol derivatives (e.g., alkandiols or cyclo alkanols); or naphtha or naphtha components. Most preferably, the solvent comprised by the coating composition is xylene, ethylbutanol, chloroform and/or acetone. The solvent may also be DMSO (dimethyl sulfoxide). In particular, DMSO may be used as a "first solvent", which is capable of dissolving at least 0.1% v/v of the coating polymer and/or the coating resin and which forms a contact angle on the polymer material surface of the article of 90° or higher when containing the coating polymer and/or resin. Such a "first solvent" is typically combined with a "second solvent" in an amount of at least 20% of said first solvent, which second solvent forms a contact angle on the polymer material surface of the article of less than 90° and which has an at least 10% longer drying time than said first solvent. If DMSO is used as a first solvent, a preferred second solvent may be, for example, dodecane.

Method for Treating a Surface

In a further aspect, the present invention also provides a method for treating a surface of an article for contacting coagulated blood or coagulated blood components made of a polymer material, comprising the step of applying a coating composition, which comprises (i) a polymer and/or a resin and (ii) a solvent, to at least a part of the surface of the article.

Accordingly, the present invention provides a method for obtaining an article according to the present invention as described above, namely by applying a coating composition to the article's body to obtain a coating material as described above. Accordingly, preferred embodiments of the article for contacting coagulated blood or coagulated blood components made of a polymer material, whose surface is at least partially to be coated with a coating composition, correspond to preferred embodiments of the article according to the present invention (in particular the article's body as described above) as described above. Accordingly, preferred embodiments of the polymer and/or the resin comprised by the coating composition (used in the method according to the present invention) correspond to preferred embodiments of the polymer and/or the resin comprised by the coating material as described above.

Moreover, since the coating material of the article according to the present invention is preferably obtained by drying a coating composition, the polymer and/or the resin comprised by the coating composition (used in the method according to the present invention) is preferably the same as the polymer and/or the resin comprised by the article's coating material as described above. In addition, preferred embodiments of the solvent as described above correspond to preferred embodiments of the solvent comprised by the coating composition (used in the method according to the present invention). Moreover, the coating composition used in the method according to the present invention is preferably the coating composition according to the present invention as described above. Accordingly, preferred embodiments of the coating composition used in the method according to the present invention include preferred embodiments of the coating composition according to the present invention as described above.

Accordingly, it is preferred that the coating composition comprises at least one polymer as described above. More preferably, the polymer comprised by the coating composition is a polymer or a copolymer comprising one or more monomers selected from styrene monomers, (meth)acrylate monomers, (meth)acrylamide monomers, alkyl monomers, vinyl monomers, allyl monomers, carbonate monomers, aromatic monomers, olefin monomers, halogenolefine monomers, methylolefine monomers, urethane monomers, amide monomers, ester monomers and ether monomers, as described above. It is also more preferred that the coating composition comprises at least one polymer or copolymer selected from polystyrenes, polycarbonates, polymethacrylates, polyolefines, polyhalogenolefines, polymethylolefines, polyurethanes, polyamides, polyesters, polyethers, any partially substituted polymers thereof, or any co-polymers thereof, as described above. Even more preferably, the polymer comprised by the coating composition is a polymer or a copolymer comprising one or more monomers selected from styrene monomers, (meth)acrylate monomers, (meth)acrylamide monomers, carbonate monomers, amide monomers, and aromatic monomers, as described above. Most preferably, the polymer comprised by the coating composition is selected from acrylonitrile butadiene styrene (ABS), methyl methacrylate acrylonitrile butadiene styrene (MABS), polystyrene (PS), high impact polystyrene (HIPS), poly(methyl methacrylate) (PMMA), polycarbonate (PC), polyamide (PA), and polyphenylene sulfide (PPS), as described above.

As described in detail above, the polymer comprised by the coating composition is preferably the same as the polymer comprised by the polymer material. Alternatively, it is also preferred that the polymer comprised by the coating composition is distinct from the polymer comprised by the polymer material, as described above in more detail.

Preferably, the coating composition comprises at least one resin as described above. More preferably, the resin is selected from epoxy resin, phenol resin, polyurethane resin and/or acrylate resin, as described above.

It is also preferred that the coating composition comprises a dye, as described in detail above. In a preferred embodiment the coating composition comprises a particle enabling determination of the quality of the coating.

As described above in more detail, the polymer material (of which the article to be coated is made) is preferably a mass-production compatible plastic. More preferably, the polymer material is selected from thermoplastics, thermoplastic elastomers, conventional elastomers, and duromers, as described above. Even more preferably, the polymer material comprises polymethylpentene (PMP) and/or methyl methacrylate acrylonitrile butadiene styrene (MABS).

Preferably, the article made of the polymeric material is produced by injection molding, press molding, extrusion molding, milling, cutting, or swiveling, preferably by injection molding.

In a preferred embodiment, the article is a measurement cup, such as a cuvette or a test cell, as described above. In another preferred embodiment the article is a probe, such as a pin, or a sleeve for a pin or probe, as described above.

As described above, it is preferred that the coating composition comprises at least one solvent selected from benzene or benzene derivatives (e.g., alkyl or polyalkyl benzenes); acetate or acetate derivatives (e.g., alkyl or polyalkyl acetates); alkanols or alkanol derivatives (e.g., alkandiols or cyclo alkanols); or naphtha or naphtha components. Preferably, the solvent comprised by the coating composition is a lower-risk solvent as described above.

Preferably, the coating composition used in the method according to the present invention is preferably the coating composition according to the present invention as described above. Accordingly, preferred embodiments of the coating composition used in the method according to the present invention include preferred embodiments of the coating composition according to the present invention as described above.

In the method according to the present invention, the coating composition is applied to at least a part of the surface of the article. Thereby, the meaning of "at least a part" of the surface of the article corresponds to that of "at least partially coated" as described above. Namely, the coating composition is applied to at least a part of the surface of the article's body and, thus, at least a part of the surface of the article's body will be covered with the coating material after performing the method according to the present invention. Preferably, the coating composition is applied to the entire surface of the article's body, in particular such that the article will be completely coated, i.e. the entire surface of the article (i.e. the article's body) will be covered with the coating material. Such articles can be easily obtained by simple and cost-effective coating procedures, for example by dipping the article into the coating composition. It is also preferred that the coating composition is only applied to a part of the article's surface, in particular such that the article will be only partially coated. Thereby, "at least a part" means that the coating composition is (at least) applied to that part or those parts of the article, which are contacted by coagulating and/or coagulated blood (components) during the articles normal use. Accordingly, in particular at least that part or those parts of the article will be coated, which are contacted by coagulating and/or coagulated blood (components) during the articles normal use. For example, if the article is a measurement cup, the coagulating and/or coagulated blood (components) typically contacts during its normal use the measurement cup's inside surface (i.e. the concave surface), whereas the measurement cup's outside surface (i.e. the convex surface) is typically not contacted by blood or blood components. Accordingly, in the case of a measurement cup "at least a part" means that the coating composition is at least applied to the measurement cup's inside surface (i.e. the concave surface). It may be preferred that the coating composition is only applied to one or more parts of the article (e.g., for the measurement cup only the inside surface), in particular if the coating material is expensive. In particular, to improve blood adhesion it is usually not necessary to coat such parts of the article's surface, which are not in contact with blood during the article's normal (intended) use. To provide another example, if the article is a pin or a sleeve for a pin, typically only its apical part ("tip", e.g. convex surface) is intended for contact with blood, whereas its shaft is usually not intended for contact with blood. Accordingly, in the case of a pin or sleeve for a pin "at least a part" means that the coating composition is at least applied to the apical part ("tip", e.g. convex surface), which may be realized, e.g. by dipping only the apical part of the pin into the coating composition.

Preferably, the coating composition is applied to at least a part of the surface of the article by spraying the coating composition onto the article, by filling the article with the coating composition, by dipping the article into the coating composition, by spin coating, by dip-tumbling, by spray-tumbling, by screen printing, by inkjet printing, by micro-contact printing, by sputter deposition, by thermal evaporation, or by vapor deposition.

If the coating composition is applied to at least a part of the surface of the article by filling the article with the coating composition, excess coating composition is typically removed after filling the article with the coating composition. Excess coating may be removed, for example, at least 1s, 2s, 3s, 4s, 5s, 6s, 7s, 8s, 9s, or 10s after filling, preferably at least 2s after filling, more preferably at least 5s after filling, and most preferably at least 10s after filling.

"Dipping" the article into the coating composition refers to (i) dipping only a part of the article into the coating composition (i.e. not the complete article, such as only the apical part of a pin) and (ii) dipping the complete article into the coating composition, such that the entire surface of the article comes in contact with the coating composition.

As used herein, "spin coating" refers to a procedure, which is typically used to deposit uniform thin films to a substrate. Usually a small amount of coating composition is applied on the center of the substrate, which is either spinning at low speed or not spinning at all. The substrate is then rotated at high speed in order to spread the coating composition by centrifugal force. A machine used for spin coating is called a spin coater, or simply spinner. Rotation is continued while the coating composition spins off the edges of the substrate, until the desired thickness of the film is achieved. The applied solvent is preferably volatile, and may simultaneously evaporate.

As used herein, "dip-tumbling" refers to a procedure, wherein the article (or parts thereof to be coated) are continuously spun in a perforated tumbler which is temporarily dipped into the coating composition.

As used herein, "spray-tumbling" refers to a procedure, wherein the article (or parts thereof to be coated) are continuously spun in a closed tumbler with a spraying unit inside.

More preferably, the coating composition is applied to at least a part of the surface of the article by spraying the coating composition onto the article, by filling the article with the coating composition, by clipping the article into the coating composition, by dip-tumbling or by spray-tumbling.

It is also preferred that the method according to the present invention comprises a step of removing excess coating composition, which directly follows after the step of applying the coating composition. Depending on how the coating composition is applied to the article's surface, the application technique may result in the presence of excess coating composition, which may be removed, for example to avoid overly thick layers of coating material (for example for cost or other reasons). For example, if the surface to be coated has a concave shape (such as the inside surface of a measurement cup), that surface may be "filled" with coating composition. After (complete) filling, excess coating composition may then be removed, for example by tilting the concave surface such that excess coating composition flows off by means of gravity. Accordingly, excess coating composition is preferably removed by means of gravity, e.g. as described above or—for articles and surfaces thereof having other shapes, including convex shapes—by leaving the article such that excess coating composition simply drips off. Other preferred options of removing excess coating composition are (i) by spinning the article, such that excess coating composition is removed by centrifugal force, and/or (ii) by using a pipette, an automated pipette or a liquid handling automat, such that excess coating is removed by aspiration into a (waste) reservoir. Any of the above techniques for removing excess coating composition may be used alone (separately) or two or more of those techniques may be combined.

Excess coating composition may be removed, for example, at least 1s, 2s, 3s, 4s, 5s, 6s, 7s, 8s, 9s, or 10s after application of the coating composition, preferably at least 2s after application of the coating composition, more preferably at least 5s after application of the coating composition, and most preferably at least 10s after application of the coating composition. It is also preferred that excess coating composition is removed during application of the coating. For example if the coating composition is applied by spin coating the rotation leads to distribution of the coating composition on the article's surface as well as to remove excess coating composition.

In particular, if a step of drying is performed, excess coating composition (if present), is preferably removed before drying to accelerate the drying process.

Preferably, the method according to the present invention comprises a step of drying the coating, which follows (directly) after the step of applying the coating composition. The step of drying may follow directly after the step of applying the coating composition (i.e. without any intermediate steps) or there may be one or more intermediate steps after the step of applying the coating composition and before the step of drying, such as a step of removing excess coating composition as described below.

In general, drying is a mass transfer process, by which a (solid) coating material is obtained from a (liquid) coating composition. In particular drying comprises the removal of the solvent from the (liquid) coating composition, usually by evaporation. Different drying methods are known and preferably the step of drying involves one or more of the following ((i)-(vi)):

(i) Natural air drying, which takes place when materials are dried at air without heating, taking advantage of the air's natural drying potential. Optionally, the (unheated) air may be forced, e.g. by a fan. Although this process may be slow, it is also the most gentle kind of drying.

(ii) Convective (or "direct") drying, in which hot air is applied. Air heating increases the driving force for heat transfer and accelerates drying. It also reduces air relative humidity, further increasing the driving force for drying. In the falling rate period, as moisture content falls, the solids heat up and the higher temperatures speed up diffusion of water from the interior of the solid to the surface. However, product quality considerations limit the applicable rise to air temperature. Excessively hot air can almost completely dehydrate the solid surface, so that its pores shrink and almost close, leading to crust formation or "case hardening", which is usually undesirable. An example of convective drying is spray drying.

(iii) Indirect or contact drying (heating through a hot wall), such as drum drying and vacuum drying. Again, higher wall temperatures will speed up drying but this is limited by product degradation or case-hardening.

(iv) Dielectric drying, in which radiofrequency or microwaves are absorbed inside the material. It may be used to assist air drying or vacuum drying. Microwave finish drying speeds up the otherwise very low drying rate at the end of the classical drying methods.

(v) Freeze drying or lyophilization, which is a drying method where the solvent is frozen prior to drying and is then sublimed, i.e., passed to the gas phase directly from the solid phase, below the melting point of the solvent. Pressure can be reduced by a high vacuum pump (though freeze drying at atmospheric pressure is possible in dry air). If a vacuum pump is used, the vapor produced by sublimation is typically removed from the system by converting it into ice in a condenser, operating at very low temperatures, outside the freeze drying chamber.

(vi) Supercritical drying (superheated steam drying), which involves steam drying of products containing water. This process is feasible because water in the product is boiled off, and joined with the drying medium, increasing its flow. It is usually employed in closed circuit and allows a proportion of latent heat to be recovered by recompression, a feature which is not possible with conventional air drying, for instance.

Preferably, the drying step involves natural air drying, convective (or "direct") drying, indirect or contact drying, dielectric drying, supercritical drying or any combination thereof. More preferably, the drying step involves natural air drying, convective (or "direct") drying, indirect or contact drying, or any combination thereof. Even more preferably, the drying step involves natural air drying and/or convective (or "direct") drying. Most preferably, the drying step involves natural air drying.

More preferably, the drying step is performed at a temperature of 4-180° C. Even more preferably, the drying step is performed at a temperature of 10-80° C. Most preferably, the step of drying is performed at room temperature (about 20° C. or about 22° C.).

Furthermore, it is preferred that the method according to the present invention further comprises a step of quality control of the coating, which follows (directly) after the step of applying the coating composition. The step of quality control of the coating may follow directly after the step of applying the coating composition (i.e. without any intermediate steps) or there may be one or more intermediate steps after the step of applying the coating composition and before the step of quality control of the coating, such as a step of removing excess coating composition as described below and/or as the step of drying as described above. Preferably, the step of quality control is performed before, during or after the step of drying. More preferably, the step of quality control is performed during or after the step of drying. Alternatively, it is also more preferred if the step of quality control is performed before the step of drying.

Preferably, the quality control of the coating is performed by optical, electrical, and/or magnetic fields, for example by light reflection, color changes, light image changes, X-ray image changes, fluorescence image changes, light emission wavelength changes, and/or magnetic field changes. To this end, the coating composition (and the coating material, respectively) may comprise a dye (e.g., coumarine, methylene blue, rhodamine, fluorescein, and/or luciferin) for optical imaging, or other particles useful for the envisaged quality control method, such as particles useful for X-ray imaging (e.g., metal particles), or magnetic particles for magnetic field imaging.

In a further aspect the present invention also provides an article for contacting coagulated blood or coagulated blood components obtainable by the method according to the present invention as described above. Such a coated article combines the advantages of (i) optimum body material with (ii) optimum coating material providing improved adhesion to blood clots. Moreover, (polymeric) surfaces obtained by coating provide improved adhesion to blood clots as compared to (polymeric) surfaces obtained by molding techniques, such as injection molding, as shown by the present examples.

Use of the Coated Article

In a further aspect the present invention also provides various uses of the article according to the present invention as described above.

Firstly, the use of the article according to the present invention as described above for contacting coagulated blood and/or coagulated blood components is provided. Due to the improved adhesion strength of coagulated blood and/or coagulated blood components to the coating of the article according to the present invention as described above, the coagulated blood and/or coagulated blood components do(es) not spill off the article's surface, but are instead "coupled" thereto by adhesive forces. This enables a wide range of applications, which involve polymeric materials contacting coagulated blood and/or coagulated blood components. For example, implants or special artery sealings would benefit from improved blood-clot anchoring at artificial surfaces. Most preferably, however, the article according to the present invention as described above is used in blood diagnostics (e.g. haemostasis analysis), in particular for blood coagulation testing.

In general, coagulation testing (also referred to as "blood clotting testing") refers to testing used for diagnostics of the hemostasis system. Preferably, coagulation testing is performed by using a coagulometer. A "coagulometer" is the medical laboratory analyzer used for testing of the hemostasis system. Modern coagulometers realize different methods of activation and observation of development of blood clots in blood or in blood plasma. Substantially all coagulometers used in laboratory diagnostics are based on the methods of testing of the hemostasis system created more than fifty years ago.

Coagulation testing preferably involves a global test and/or a local test.

Global tests characterize the results of work of the whole clotting cascade. They suit to diagnose the general state of the blood coagulation system and the intensity of pathologies, and to simultaneously record all attendant influences. Global methods play the key role at the first stage of diagnostics: they provide an integral picture of alterations within the coagulation system and allow predicting a tendency to hyper- or hypo-coagulation in general. Preferred examples of global tests include thromboelastography, thrombin generation tests (thrombin potential, endogenous thrombin potential) and thrombodynamics tests.

Local tests characterize the results of work of the separate components of the blood coagulation system cascade, as well as of the separate coagulation factors. They are essential for the possibility to specify the pathology localization within the accuracy of coagulation factor. A D-dimer (product of thrombi degradation) test can be specified separately. The rise of D-dimers concentration in the patient's blood states the possibility of the completed thrombosis. To obtain a complete picture of the work of hemostasis by a patient, the doctor should have a possibility to choose which test is necessary. Preferred local tests include tests in platelet poor plasma or in platelet free plasma (convenient for transportation; can be frozen; possibility to use optical observation methods; but the thrombocyte component of the hemostasis is not taken into account), tests in platelet rich plasma (close to real conditions in the body, but restrictions as to the terms of work), and tests in whole blood (the most adjusted to human physiology; the test can be started immediately; but the least convenient due to terms of blood storage and difficulties of the results' interpretation). Preferred examples of local tests include (activated) partial thromboplastin time (PTT, APTT), prothrombin time test (or prothrombin test, INR, PT), and highly specialized methods to reveal the alteration in concentration of separate factors.

Most preferably, the article according to the present invention as described above is used in viscoelastic measurements. Viscoelastic measurement methods and devices are described in detail in U.S. Pat. No. 5,777,215 A, in U.S. Pat. No. 6,537,819 B2, and in U.S. Pat. No. 8,383,045 B2.

BRIEF DESCRIPTION OF THE FIGURES

In the following a brief description of the appended figures will be given. The figures are intended to illustrate the present invention in more detail. However, they are not intended to limit the subject matter of the invention in any way.

EXAMPLES

In the following, particular examples illustrating various embodiments and aspects of the invention are presented. However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Coating of Various Articles and Functionality Tests

Figure 8:
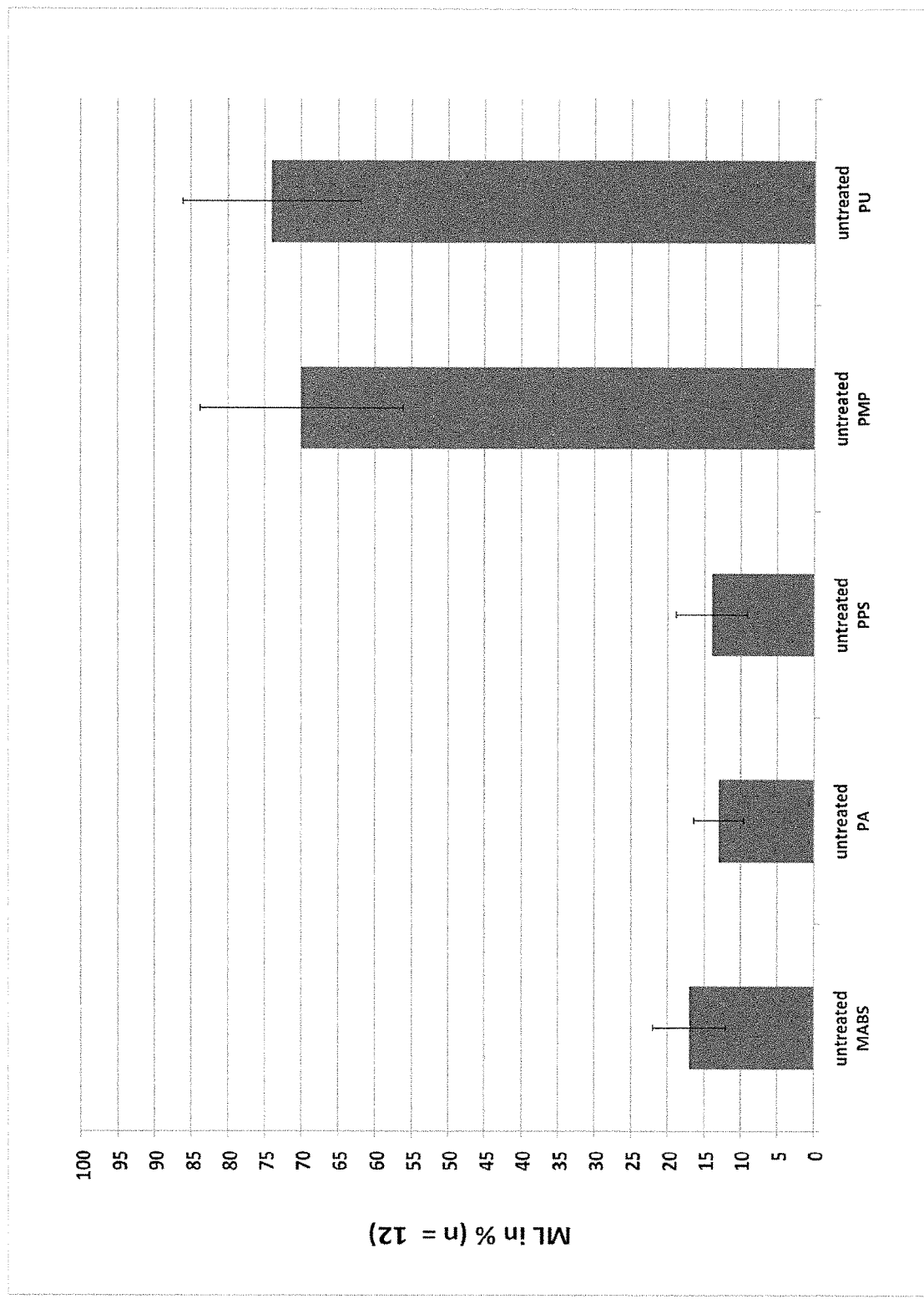
FIG. 8: shows for Example 2 maximum lysis activity (ML, % ratio between clot firmness 60 minutes after measurement start and maximum clot firmness) in thromboelastometric measurements of different untreated articles (cuvettes and probes) made of polymethylpentene (PMP), methyl methacrylate acrylonitrile butadiene styrene (MABS), polyamide (PA), polyphenylene sulfide (PPS), or polyurethane (PU). The mean and standard deviation values were obtained from 8 individual measurements with one blood sample.

In the following examples, several exemplary results obtained with different articles according to the present invention (summarized, e.g., in FIG. 8-10) will be described. To obtain an article according to the present invention, an uncoated article made of a first polymer material was coated by using a coating composition as described below.

In general, to obtain the coating compositions, the following solvents were used to dissolve 500 mg of each raw polymer material in 5 ml solvent (for detailed description see the examples below):

Acrylonitrile butadiene styrene (ABS; Terluran GP-22, INEOS Styrolution Group GmbH, Germany) was dissolved in 96% xylene;

Methyl methacrylate acrylonitrile butadiene styrene (MABS; TERLUX® 2802, INEOS Styrolution Group GmbH, Germany) was dissolved in 96% xylene or in ethylbutanol (Sigma-Aldrich Chemie GmbH, Germany) as indicated;

High impact polystyrene (HIPS; Styrolution PS 495N, INEOS Styrolution Group GmbH, German)) was dissolved in 96% xylene;

Poly(methyl methacrylate) (PMMA; Plexiglas®, EVONIK Industries AG, Germany) was dissolved in 96% acetone;

Polycarbonate (PC; Lexan™ 144R, Germany) was dissolved in 96% chloroform;

Polyamide (PA; Trogamid® T5000, Evonik Industries AG, Germany) was dissolved in 96% DMSO, but the solution was not properly applicable as coating composition due to the high polarity of DMSO; and polyurethane (PU; Desmopan® 385 S, Bayer MaterialScience AG, Germany) was dissolved in 96% DMSO, but the solution was not properly applicable as coating composition due to the high polarity of DMSO.

In general, in the experiments explained in detail below, similar results were obtained for the solvents xylene, ethylbutanol, or a combination thereof (e.g., 50:50).

To achieve sufficient coating of all surface areas that are in blood contact during a thromboelastographic measurement, articles to be coated (cuvettes and probes) were either (i) filled with 600 µl of the coating composition and excess coating composition was removed after about 10 s (cuvettes), or (ii) dipped into the coating composition for about 2 s (probes). Articles (cuvettes and probes) were subsequently dried in air for about 1 hour.

In general, improvements of blood adhesion to the polymeric surfaces of articles used for thrombelastographic diagnostics by applying coatings according to the present invention can be detected by comparing the initially achieved maximum clot firmness with the reduction of clot firmness at the end of the measurement (e.g., 60 min after measurement start). This ratio, also called "ML" parameter (maximum lysis activity, ML; % ratio between (i) clot firmness at the end of measurement, for example 60 minutes after measurement start, and (ii) maximum clot firmness), can be artificially lowered by partial ruptures of the fibrin network from the surface during measurements (see FIG. 7). Since the ML parameter is often used for the diagnosis of hyperfibrinolytic activity in the coagulation system of a patient blood sample, lower values due to insufficient surface adhesion of the fibrin network are a potential risk in haemostasis analysis. Since the blood of patients with considerably increased platelet content tends to tear off the surface due to denser clot packing, mistakable measurements cannot be excluded. By applying coatings for the articles according to the present invention, this drawback of unwanted tear-offs can be satisfactorily eliminated (see also the following examples and FIG. 8-10). It can also appear that the tear-off of a blood clot starts even before the maximum clot firmness is achieved in the measurement (maximum clot firmness is typically achieved about 20-30 minutes after initial clotting). In this case, the ML parameter might be less influenced by the tear-off, but the clot firmness amplitude measured 20 minutes after initial clotting (called parameter A20) will be reduced. Accordingly, occurrence of an unwanted tear-off of the blood clot from the article surface can either be detected by a higher ML parameter and/or a lower A20 parameter when comparing to an article with improved surface adhesion of the blood clot. Therefore, higher ML values (as compared to a reference) and/or lower A20 values (as compared to a reference) indicate increased adhesion to clotting blood (as compared to the reference).

The functionality was assessed by comparing thrombelastographic measurements performed with ROTEG® 05 devices (Pentapharm GmbH, Germany), where differently treated articles with dimensions comparable to the corresponding original measurement articles (ROTEM® Cup&Pin Pro, Tem International GmbH, Germany) were compared regarding clot firmness amplitudes after 20 minutes (A20) and maximum lysis activity (ML; % ratio between clot firmness 60 minutes after measurement start and maximum clot firmness).

Measurements were performed by pipetting 20 µl of extrinsic activator (ex-TEM®, Tem International GmbH, Germany) and 20 µl of 200 mM $CaCl_2$ (star-TEM®, Tem International GmbH, Germany) to a 300 µl citrated blood sample and transferring it to the respective article.

Example 2: Comparison of Uncoated Articles

Figure 1:
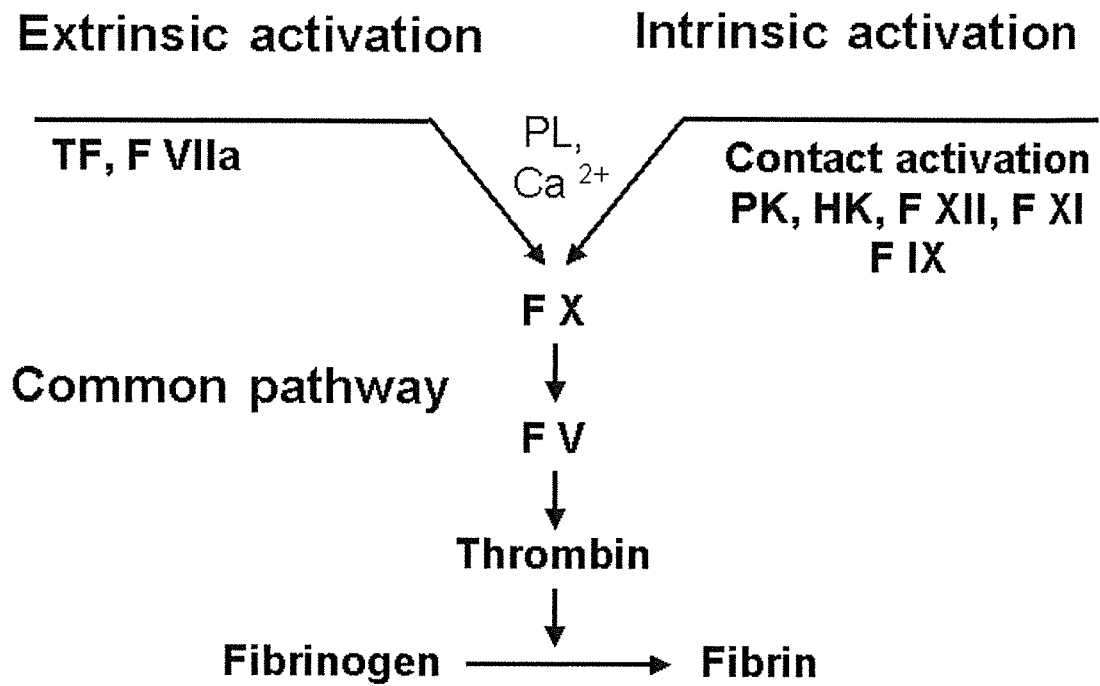
FIG. 1: shows the pathway of blood coagulation resulting in the formation of fibrin strands after either extrinsic or intrinsic activation. The different enzymatic factors are indicated by their common short names.
Figure 2:
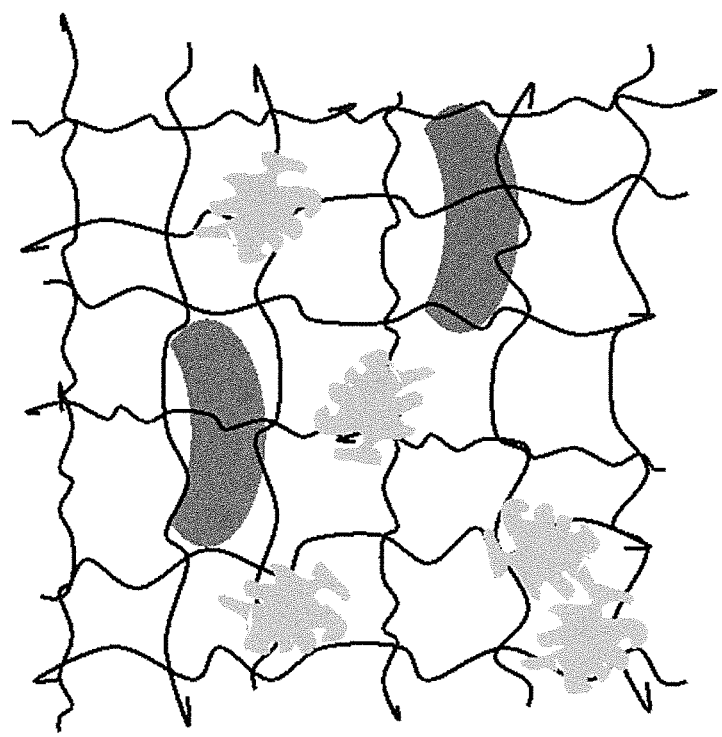
FIG. 2: Schematic representation of the blood-clot structure including fibrin strands (black), activated thrombocytes (light gray), and erythrocytes (dark gray).
Figure 3:
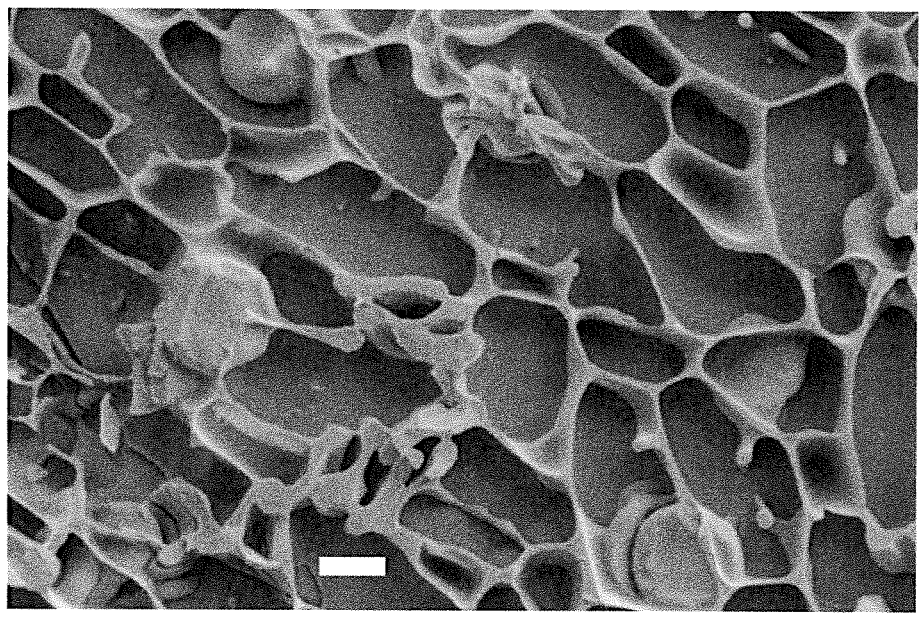
FIG. 3: Scanning electron microscopy image of coagulated blood consisting of fibrin strands, activated thrombocytes and erythrocytes. The white bar indicates a length of 5 μm.
Figure 4:
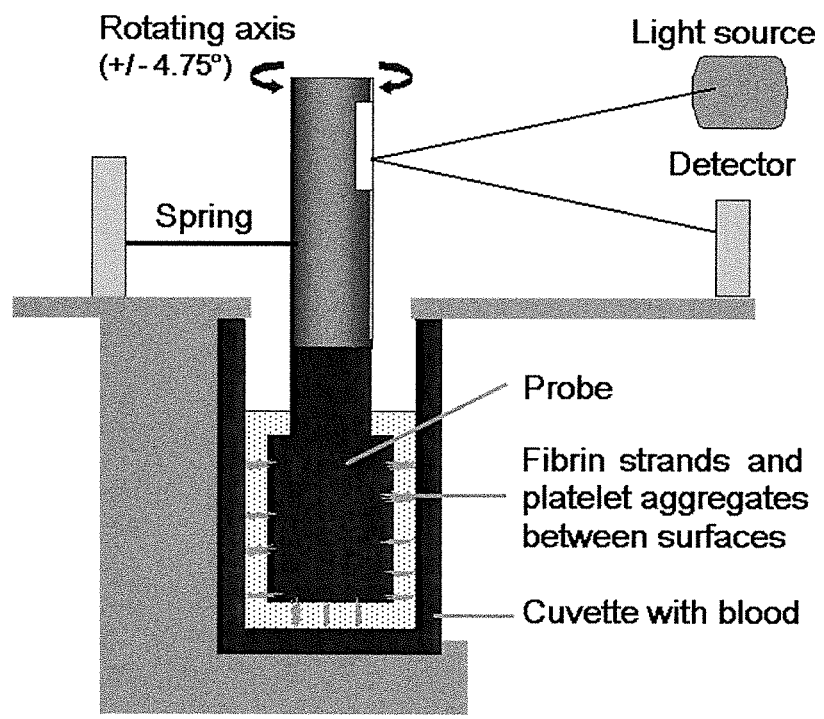
FIG. 4: shows a schematic drawing of a thromboelastometric device measuring the clot formation of coagulating blood by sensing the increasing shear modulus via a spring-driven oscillation in small angle ranges. After the formation of the clot between cup ("cuvette") and pin ("probe"), the clot itself is stretched by the movement of the pin relative to the cup. The detection of the characteristic parameters of the clot is based on the mechanical coupling of cup and pin by the clot (fibrin strands and platelet aggregates between pin and cup surfaces). This is only possible if the clot adheres on the surfaces of both, cup and pin. Thus, a firm adhesion to the surfaces of both cup and pin is typically required for viscoelastic analysis. During a viscoelastic measurement, the pin is fixed to the rotating axis and gently and slowly rotated in the cup via the spring. The axis itself is fixed to a base plate, e.g. by a ball bearing. The movement of the pin is measured optically by illuminating a mirror (fixed to the rotating axis) by use of a light source and detecting the reflected signal at the spatially resolving photo detector.
Figure 5:
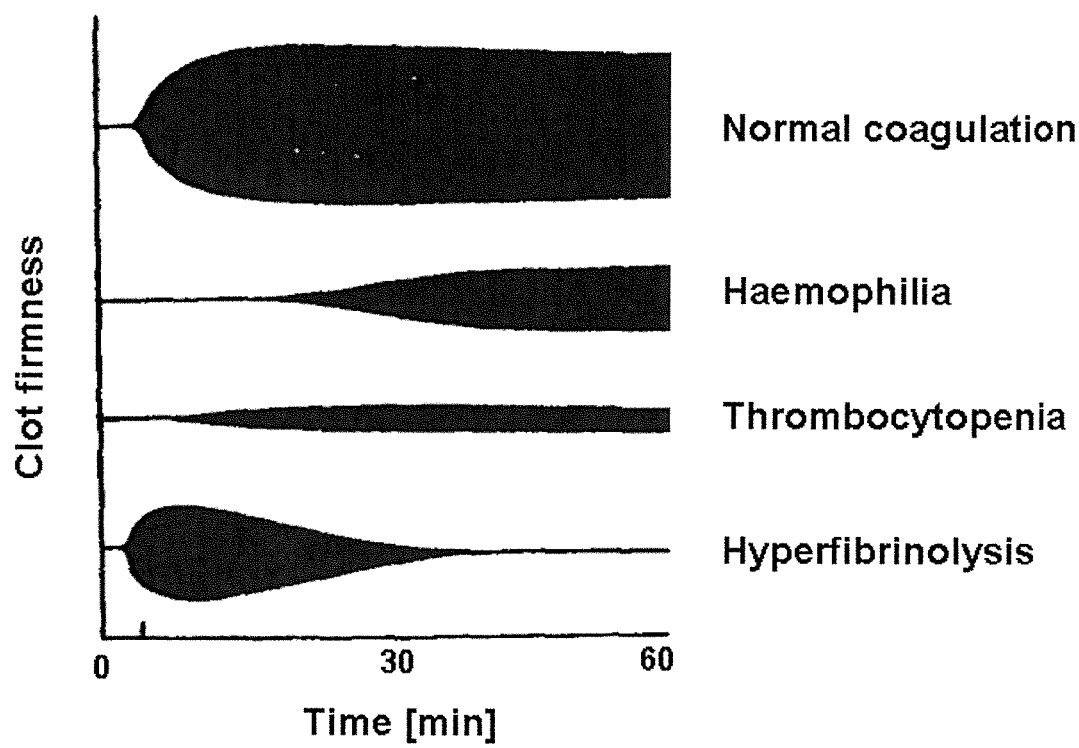
FIG. 5: Different shapes of thromboelastometric measurements indicating normal coagulation behavior and three typical disease patterns.
Figure 6:
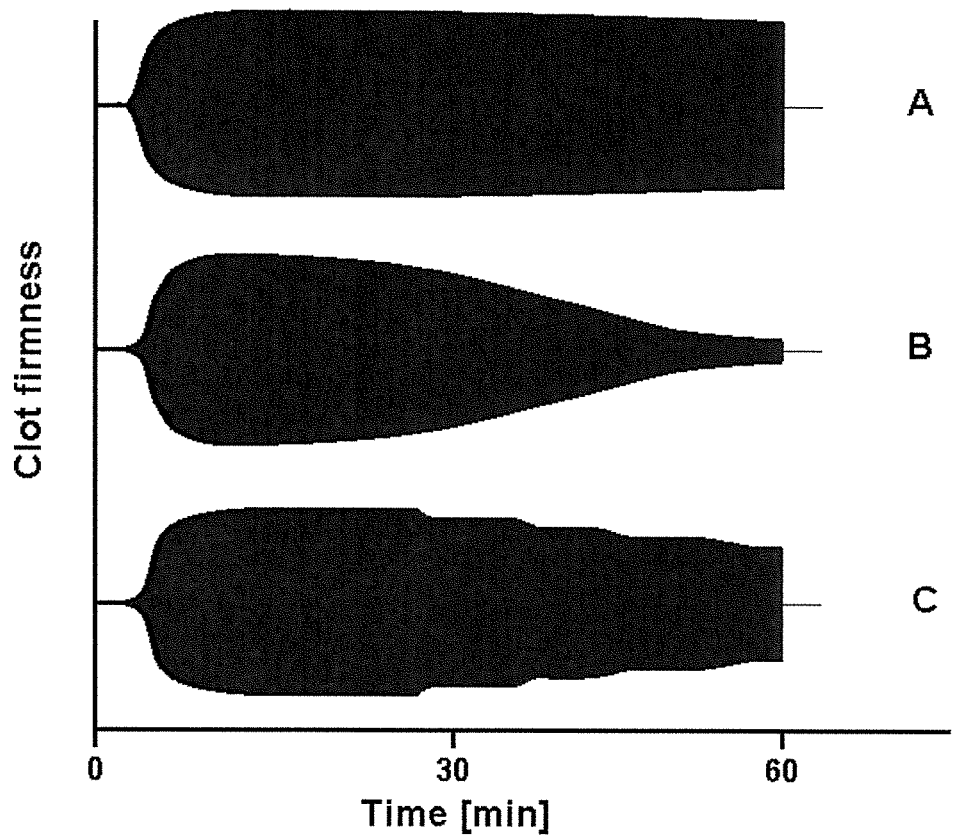
FIG. 6: Comparison of the thromboelastic patterns in the case of normal coagulation (A), pathologic hyperfibrinolysis (B), and artificial fibrin network tear-offs (C).
Figure 7:
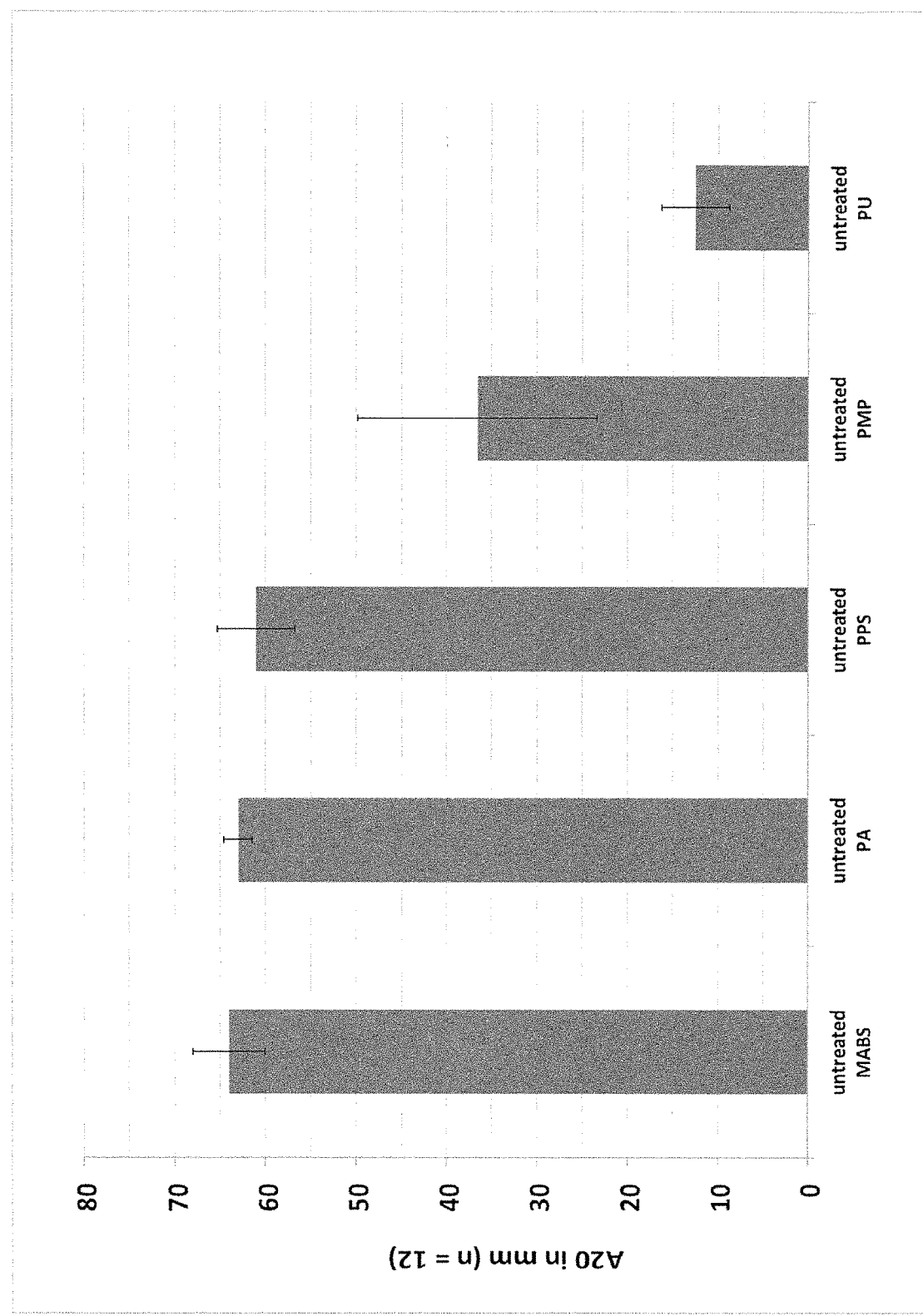
FIG. 7: shows for Example 2 clot firmness amplitude after 20 minutes (A20) in thromboelastometric measurements of different untreated articles (cuvettes and probes) made of polymethylpentene (PMP), methyl methacrylate acrylonitrile butadiene styrene (MABS), polyamide (PA), polyphenylene sulfide (PPS), or polyurethane (PU). The mean and standard deviation values were obtained from 8 individual measurements with one blood sample.

In order to efficiently determine and compare the surface characteristics regarding blood adhesion of various polymer materials, untreated/uncoated articles (cups and pins) made of polymethylpentene (PMP; TPX®, Mitsui & Co. Ltd., Japan), methyl methacrylate acrylonitrile butadiene styrene (MABS; Terlux® 2802, INEOS Styrolution Group GmbH, Germany), polyamide (PA; Trogamid® T5000, Evonik Industries AG, Germany), polyphenylene sulfide (PPS; Ryton® R-4, SOLVAY GmbH, Germany), or polyurethane (PU; Desmopan® 385 S, Bayer MaterialScience AG, Germany) were obtained by industrial injection molding. Those untreated/uncoated articles underwent functionality testing as described above (cf. Example 1). Results are shown in FIGS. 7 (clot firmness amplitudes after 20 minutes; A20) and 8 (maximum lysis activity; ML).

Injection-molded articles made of MABS, PA or PPS show significantly higher A20 values and significantly lower ML values as compared to injection-molded articles made of PMP or PU (FIG. 7, 8). Those results indicate that MABS, PA or PPS represent suitable coating polymers, which can improve surface adhesion to clotting blood, in particular if a suitable nonpolar solvent is used. Examples of such a suitable non-polar solvents are the "lower risk" solvents n-propanol (in particular for PA), xylene (in particular for MABS) and/or ethylbutanol for (in particular for MABS).

Articles made of PMP or PU without any treatment or coating show poor results regarding blood clot adhesion as indicated by comparably low A20 values and comparably high ML mean values in thromboelastometric measurements (FIG. 7, 8).

Example 3: Coating of an Exemplary Article Made of Polymethylpentene (PMP)

Uncoated articles (cup and pin) made of polymethylpentene (PMP; TPX®, Mitsui & Co. Ltd., Japan) was obtained by industrial injection molding. The uncoated articles were then partially coated with MABS (in ethylbutanol).

Figure 9:
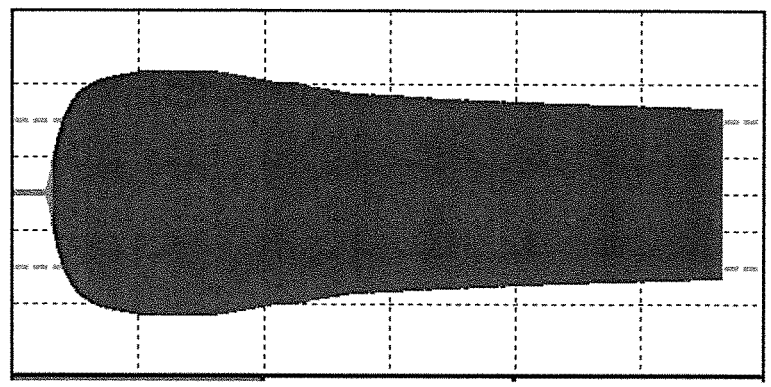
FIG. 9: shows for Example 3 a typical thromboelastography trace of an untreated/uncoated article (cuvette and probe) made of Polymethylpentene (PMP) and reflecting partial 'tear-offs' (A) in comparison to the typical thromboelastography trace obtained with an article made of identical material (PMP), but coated with MABS (B).
Figure 9:
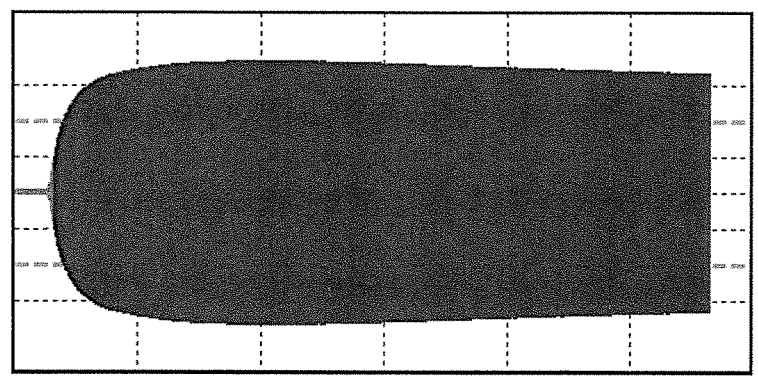

Thereafter, the article coated with MABS as well as an uncoated article (made of polymethylpentene (PMP; TPX®, Mitsui & Co. Ltd., Japan)) underwent functionality testing as described above (Example 1), whereby instead of A20 and ML parameters, typical thromboelastography traces were obtained as shown in FIG. 9.

The thromboelastography trace of the untreated/uncoated article (cuvette and probe) made of Polymethylpentene (PMP; TPX®, Mitsui & Co. Ltd., Japan) is shown in FIG. 9A. This thromboelastography trace of the untreated/uncoated article reflects partial "tear-offs" (FIG. 9A), whereas the thromboelastography trace obtained with an article made of identical material (PMP; TPX®, Mitsui & Co. Ltd., Japan), but coated with a coating composition according to the present invention, which comprises MABS (Terlux®, INEOS Styrolution Group GmbH, Germany), shown in FIG. 9B shows no such "tear-offs" (FIG. 9B).

In summary, the uncoated ("untreated") articles made of PMP shows undesired "tear-offs" (FIG. 9A), whereas those undesired "tear-offs" were abolished if the article was coated with MABS (FIG. 9B). This result demonstrates the improved surface functionality regarding clot adhesion as provided by the polymer coated onto the surface of the article.

Example 4: Coating of Further Articles Made of Polymethylpentene (PMP)

To determine blood clot adhesion of different coatings, uncoated articles (cups and pins) made of polymethylpentene (PMP; TPX®, Mitsui & Co. Ltd., Japan) were obtained by industrial injection molding and were partially coated with MABS (in xylene), HIPS, ABS, PMMA, or PC as described above (cf. Example 1).

Alternatively, uncoated articles were treated with a xylol/ethylbutanol solvent mixture (50 vol.-% xylol; 50 vol.-% ethylbutanol) without any polymer dissolved. Those articles served as comparative example to evaluate the effects of the "coating" with pure solvent (i.e., without any polymer contained therein).

Figure 10:
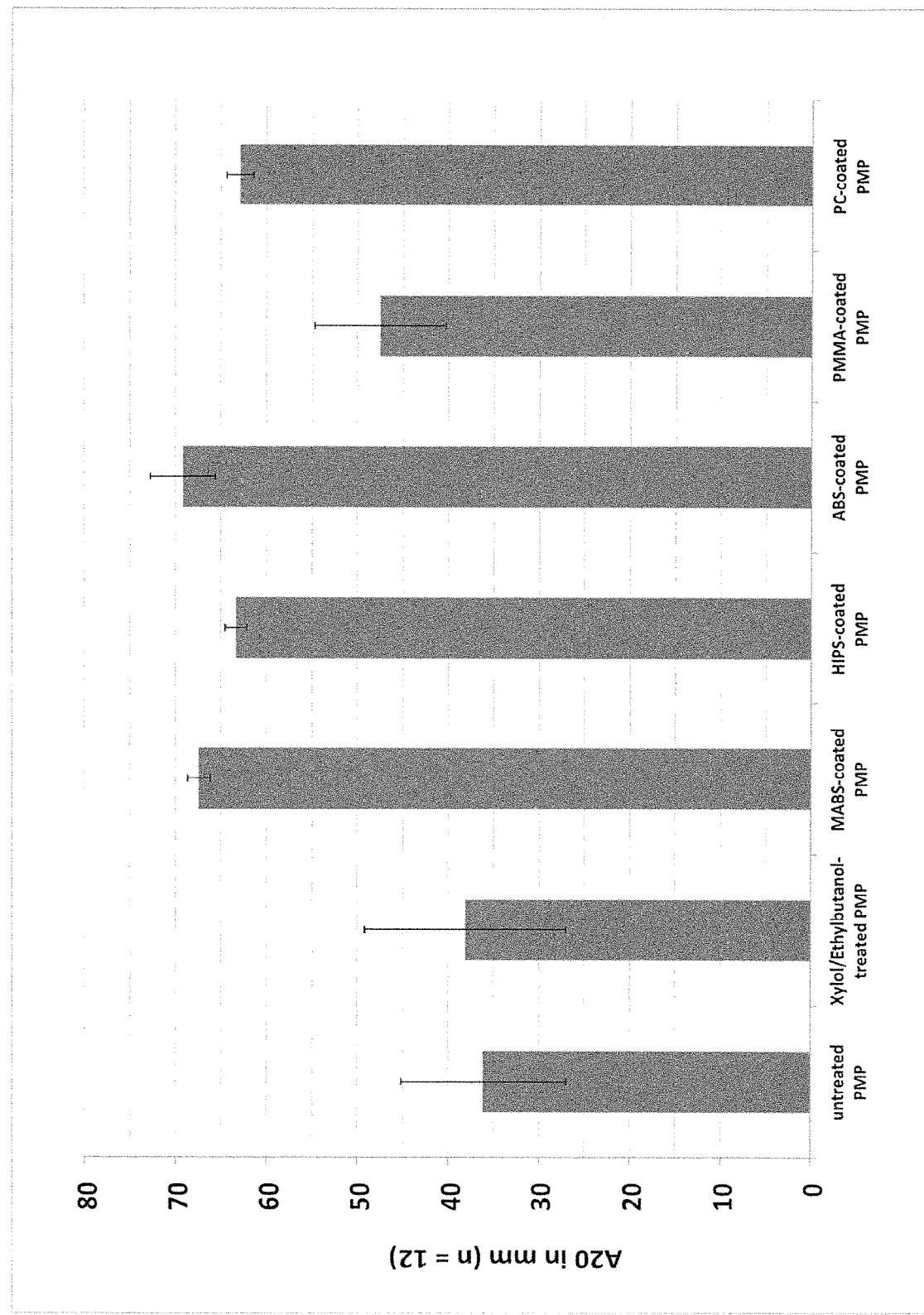
FIG. 10: shows for Example 4 clot firmness amplitude after 20 minutes (A20) in thromboelastometric measurements of differently treated/coated articles (cuvettes and probes) made of PMP. The mean and standard deviation values were obtained from 12 individual measurements with one blood sample.
Figure 11:
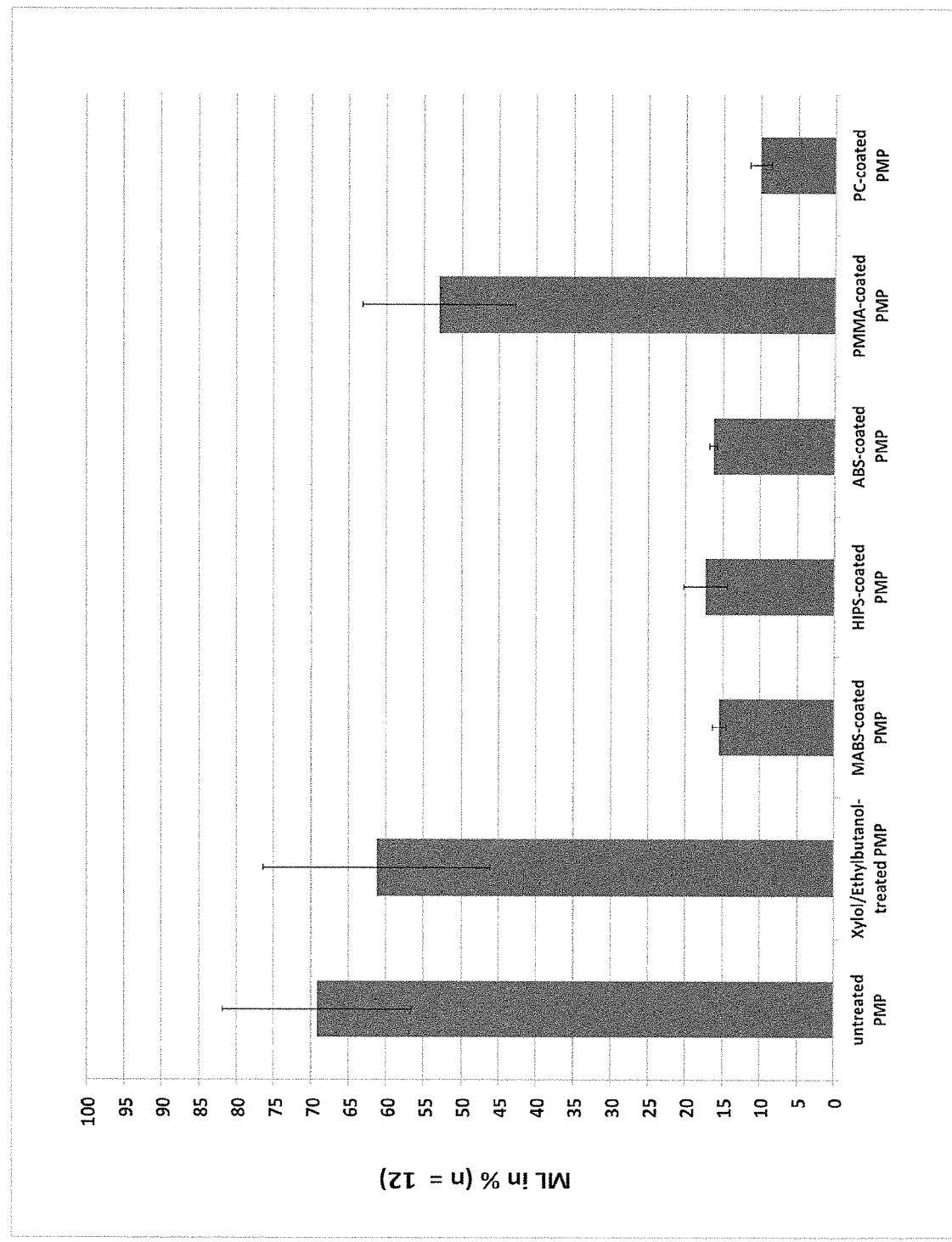
FIG. 11: shows for Example 4 maximum lysis activity (ML, % ratio between clot firmness 60 minutes after measurement start and maximum clot firmness) in thromboelastometric measurements of differently treated/coated articles (cuvettes and probes) made of PMP. The mean and standard deviation values were obtained from 12 individual measurements with one blood sample.

Thereafter, PMP articles coated with MABS, HIPS, ABS, PMMA or PC; PMP articles treated with xylol/ethylbutanol; and uncoated PMP articles underwent functionality testing as described above (cf. Example 1). Results are shown in FIGS. 10 (clot firmness amplitudes after 20 minutes; A20) and 11 (maximum lysis activity; ML).

In summary, uncoated ("untreated") articles made of PMP show lower mean values for A20 and higher mean values for ML as compared to PMP articles coated with MABS, HIPS, ABS, PMMA, or PC. Accordingly, surface coating with MABS, HIPS, ABS, PMMA or PC resulted in considerable improvements regarding A20 and ML parameters as compared to uncoated PMP articles (FIG. 10, 11). The most pronounced and significant improvements were obtained with a coating comprising MABS, HIPS, ABS or PC.

Surface treatment of PMP articles with compositions comprising the solvent only (but no polymer) resulted in A20 and ML values comparable to those of untreated/uncoated articles (FIG. 10, 11). This result demonstrates that the improved surface functionality regarding clot adhesion is indeed provided by the polymer coated onto the surface of the articles and largely independent from the solvent used.

Example 5: Coating of Articles Made of Methyl Methacrylate Acrylonitrile Butadiene Styrene (MABS)

To determine whether articles made of materials, which already show good blood clot adhesion, can be further improved by applying a coating, uncoated articles (cups and pins) made of methyl methacrylate acrylonitrile butadiene styrene (MABS; Terlux® 2802, INEOS Styrolution Group GmbH, Germany) were obtained by industrial injection molding and were coated with MABS (in xylene) or ABS as described above.

Figure 12:
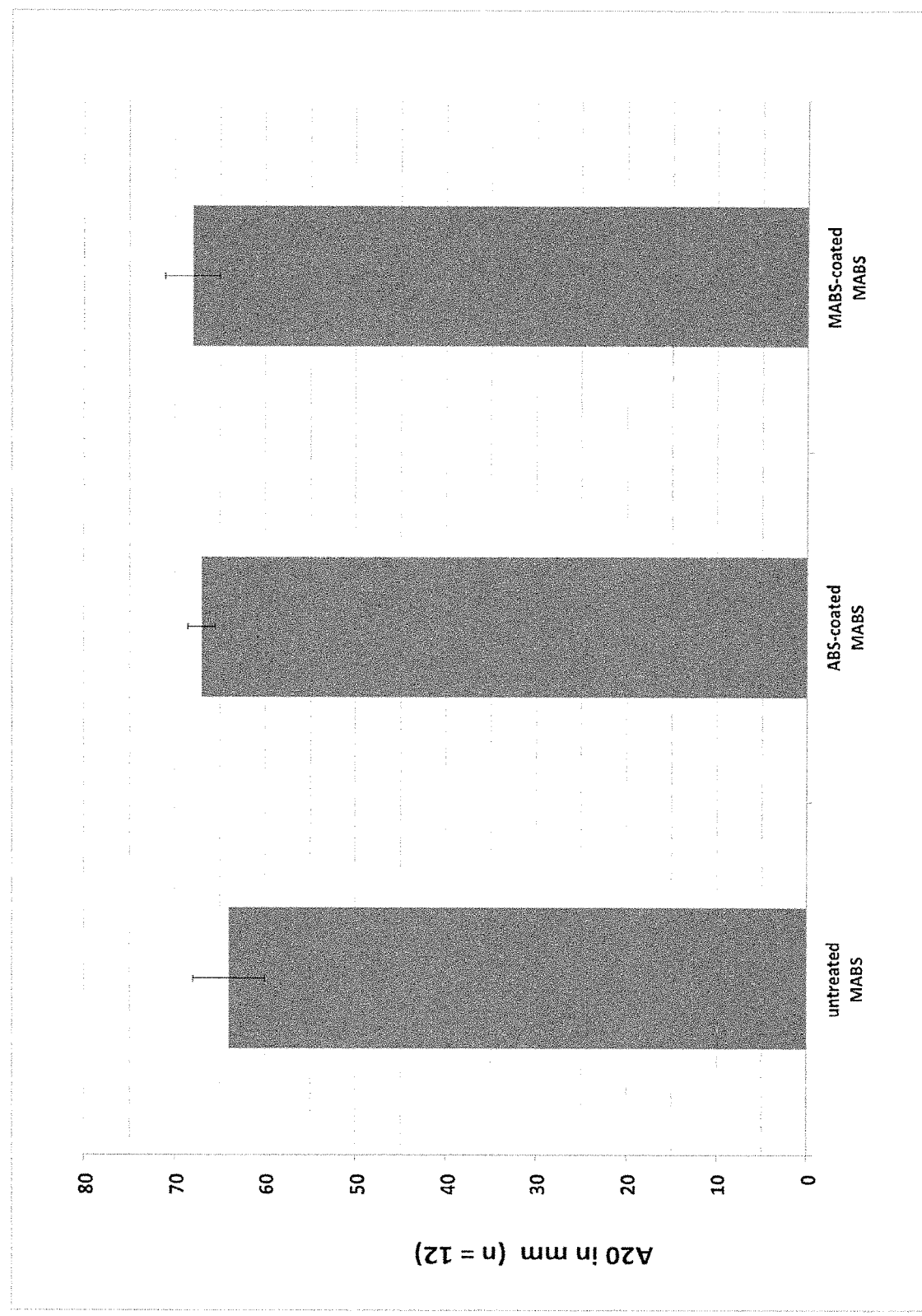
FIG. 12: shows for Example 5 clot firmness amplitude after 20 minutes (A20) in thromboelastometric measurements of differently coated articles (cuvettes and probes) made of MABS. The mean and standard deviation values were obtained from 12 individual measurements with one blood sample.
Figure 13:
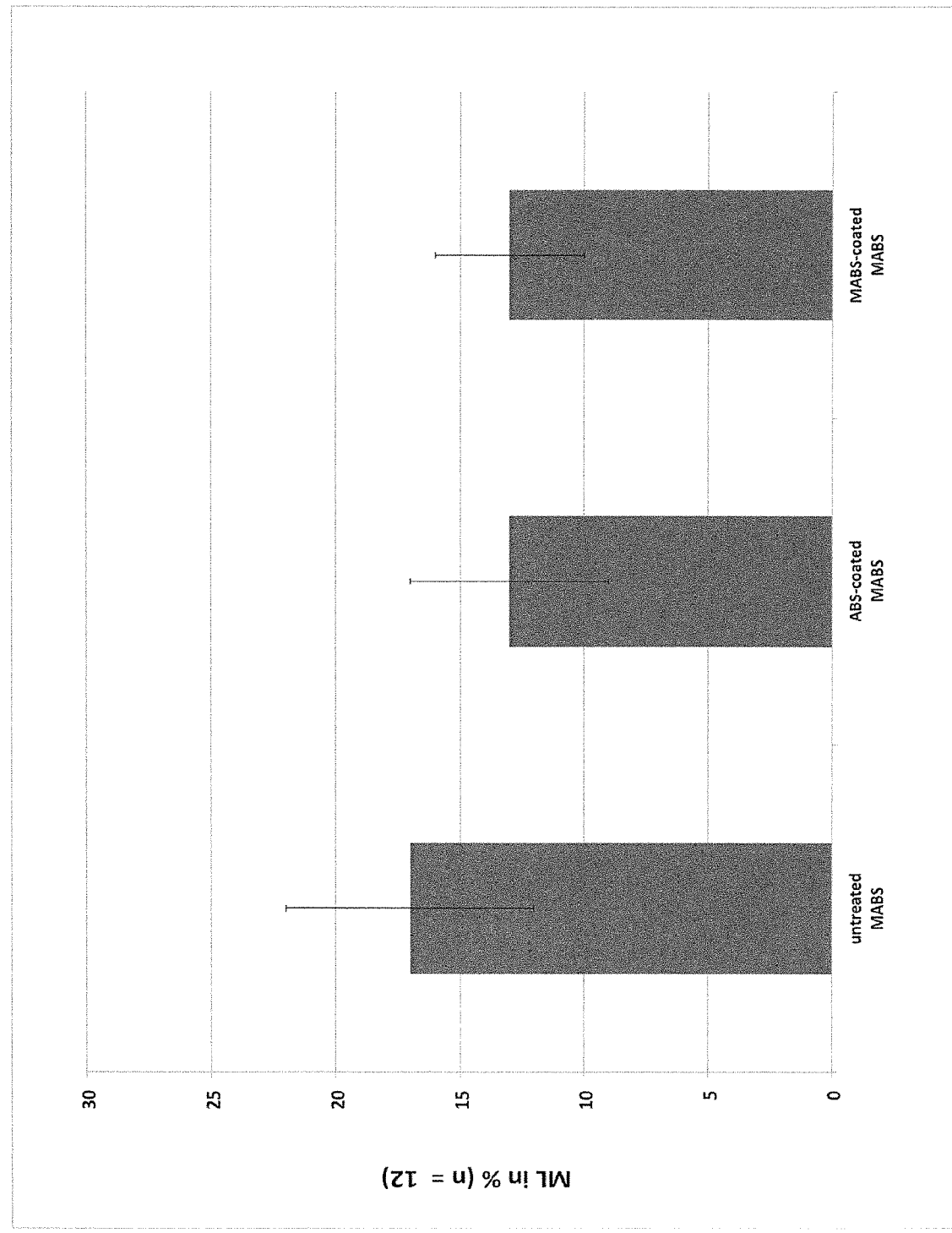
FIG. 13: shows for Example 5 maximum lysis activity (ML, % ratio between clot firmness 60 minutes after measurement start and maximum clot firmness) in thromboelastometric measurements of differently coated articles (cuvettes and probes) made of MABS. The mean and standard deviation values were obtained from 12 individual measurements with one blood sample.

Thereafter, MABS articles coated with MABS (in xylene) or ABS as well as uncoated articles underwent functionality testing as described above. Results are shown in FIGS. 12 (clot firmness amplitudes after 20 minutes; A20) and 13 (maximum lysis activity; ML).

In summary, uncoated ("untreated") articles made of MABS show lower mean values for A20 and higher mean values for ML as compared to MABS articles coated with MABS or ABS. Accordingly, surface coating with MABS or ABS resulted in improvements regarding A20 and ML when compared to uncoated MABS articles (FIG. 12, 13). However, due to the already quite good surface properties of MABS itself, the effects of the coatings are less pronounced as compared to articles made of PMP (cf. example 4).

Surprisingly, coating of articles made of MABS (Terlux® 2802, INEOS Styrolution Group GmbH, Germany) with exactly the same MABS material dissolved in xylene (and/or ethylbutanol) also resulted in significant improvements regarding A20 and ML (see FIG. 12, 13). These results imply that the surface properties regarding blood adhesion are not only improved by using a coating material providing better surface properties than the material of the uncoated article, but also by the process of coating. Namely, coating with a dissolved polymer provides improved surface characteristics as compared to injection molding of the same material. Without being limited thereto, the inventors assume that a potential reason may be a different alignment of molecules on the surface (e.g., randomly vs. ordered), or the appearance of impurities on the surface of injection-molded surfaces due to lubricant residuals of the molding machinery.

The invention claimed is:

1. A pair of first and second disposable articles adapted for use in a viscoelastic measurement apparatus for measuring coagulation characteristics of a blood sample, the first and second disposable articles being adapted to move with respect to each other, a volume being defined between surfaces of the first and second disposable articles, the volume adapted to receive the sample of blood, each of the first and second disposable articles comprising:
(a) an article body made of a polymer material, the polymer material comprising a first polymer, and
(b) a coating material layer, distinct from the article body, disposed on the surfaces defining the volume adapted to receive the sample of blood, the coating material layer comprising a coating material selected from the group consisting of a second polymer, a resin, and combinations thereof, the coating material layer being configured to adhere to a fibrin network during coagulation of the blood sample;
wherein,
(i) the first disposable article is a measurement cup,
(ii) the second disposable article is selected from the group consisting of a pin and a sleeve for a pin, and (iii) the measurement apparatus is selected from the group consisting of a thromboelastography measurement apparatus and a thromboelastometry measurement apparatus.

2. The pair of disposable articles according to claim 1, wherein the coating material comprises at least one second polymer.

3. The pair of disposable articles according to claim 2, wherein the second polymer comprises a monomer selected from the group consisting of a styrene monomer, a (meth)acrylate monomer, a (meth)acrylamide monomer, an alkyl monomer, a vinyl monomer, an ally I monomer, a carbonate monomer, an aromatic monomer, an olefin monomer, a halogenolefine monomer, a methylolefine monomer, a urethane monomer, an amide monomer, an ester monomer, and an ether monomer.

4. The pair of disposable articles according to claim 2, wherein the second polymer is selected from the group consisting of a polystyrene, a polycarbonate, a polymethacrylate, a polyolefine, a polyhalogenolefine, a polymethylolefine, a polyacetal a polyurethane, a polyamide, a polyaramide, a polyester, a polyether, a polyketone, partially substituted polymers of any of the foregoing, and co-polymers of any of the foregoing.

5. The pair of disposable articles according to claim 2, wherein the second polymer comprises a monomer selected from the group consisting of a styrene monomer, a (meth)acrylate monomer, a (meth)acrylamide monomer, a carbonate monomer, an amide monomer, and an aromatic monomer.

6. The pair of disposable articles according to claim 2, wherein the second polymer is selected from the group consisting of acrylonitrile butadiene styrene (ABS), methyl methacrylate acrylonitrile butadiene styrene (MABS), polystyrene (PS), high impact polystyrene (HIPS), poly(methyl methacrylate) (PMMA), polycarbonate (PC), polyamide (PA), and polyphenylene sulfide (PPS).

7. The pair of disposable articles according to claim 2, wherein the first polymer is the same as the second polymer.

8. The pair of disposable articles according to claim 2, wherein the first polymer is distinct from the second polymer.

9. The pair of disposable articles according to claim 1, wherein the coating material comprises at least one resin.

10. The pair of disposable articles according to claim 9, wherein the resin is selected from the group consisting of an epoxy resin, a phenol resin, a polyurethane resin, an acrylate resin, and combinations thereof.

11. The pair of disposable articles according to claim 1, wherein the coating material further comprises a dye.

12. The pair of disposable articles according to claim 1, wherein the coating material further comprises a particle enabling determination of the quality of the coating material layer.

13. The pair of disposable articles according to claim 1, wherein the first polymer is a mass-production compatible plastic.

14. The pair of disposable articles according to claim 1, wherein the first polymer is selected from the group consisting of a thermoplastic, a thermoplastic elastomer, a conventional elastomer, and a duromer.

15. The pair of disposable articles according to claim 1, wherein the first polymer is selected from the group consisting of polymethylpentene (PMP), methyl methacrylate acrylonitrile butadiene styrene (MABS), and combinations thereof.

16. The pair of disposable articles according to claim 1, wherein the coating material layer is 100 nm to 100 μm in thickness.

* * * * *